(12) United States Patent
Yan et al.

(10) Patent No.: US 11,401,952 B2
(45) Date of Patent: *Aug. 2, 2022

(54) WASTE LIQUID TREATMENT APPARATUS, METHOD AND SAMPLE ANALYZER

(71) Applicant: SHENZHEN MINDRAY BIO-MEDICAL ELECTRONICS CO., LTD., Shenzhen (CN)

(72) Inventors: Yufeng Yan, Shenzhen (CN); Huilin Shi, Shenzhen (CN)

(73) Assignee: SHENZHEN MINDRAY BIO-MEDICAL ELECTRONICS CO., LTD., Shenzhen (CN)

(*) Notice: Subject to any disclaimer, the term of this patent is extended or adjusted under 35 U.S.C. 154(b) by 188 days.

This patent is subject to a terminal disclaimer.

(21) Appl. No.: 16/899,511

(22) Filed: Jun. 11, 2020

(65) Prior Publication Data
US 2020/0300272 A1 Sep. 24, 2020

Related U.S. Application Data

(63) Continuation of application No. PCT/CN2017/120372, filed on Dec. 30, 2017.

(51) Int. Cl.
*F04F 1/06* (2006.01)
*C02F 1/461* (2006.01)
(Continued)

(52) U.S. Cl.
CPC ............ *F04F 1/06* (2013.01); *C02F 1/46109* (2013.01); *G01N 33/5302* (2013.01);
(Continued)

(58) Field of Classification Search
CPC ............ C02F 1/46109; C02F 2103/003; C02F 2201/005; C02F 2209/42; F04F 1/06;
(Continued)

(56) References Cited

U.S. PATENT DOCUMENTS

2020/0386779 A1* 12/2020 Inaba ............... G01N 35/00613

FOREIGN PATENT DOCUMENTS

| CN | 102370561 A | 3/2012 |
| CN | 203281582 U | 11/2013 |

(Continued)

OTHER PUBLICATIONS

English machine translation of the description of CN 206570074 U downloaded from the European webite. (Year: 2017).*

(Continued)

*Primary Examiner* — Terry K Cecil

(74) *Attorney, Agent, or Firm* — Kory D. Christensen

(57) ABSTRACT

A waste liquid treatment apparatus, a method, and a sample analyzer are provided. The waste liquid treatment apparatus is used for treating waste liquids in waste liquid pipes, and includes at least two waste liquid chambers, a pressure supply device, and a control device. Each waste liquid chamber communicates with at least one waste liquid pipe, and is used for collecting the waste liquid in the waste liquid pipe connected thereto when the inside of the waste liquid treatment chamber is in a negative pressure state. The pressure supply device is connected to each waste liquid chamber, and the control device is configured for controlling the pressure supply device to supply air pressure to each waste liquid chamber, so that the inside of at least one waste liquid chamber is in a negative pressure state at any time during waste liquid treatment, thereby effectively shortening a waste liquid treatment cycle.

20 Claims, 10 Drawing Sheets

(51) Int. Cl.
*G01N 33/53* (2006.01)
*C02F 103/00* (2006.01)

(52) U.S. Cl.
CPC .. *C02F 2103/003* (2013.01); *C02F 2201/005* (2013.01); *C02F 2209/42* (2013.01)

(58) Field of Classification Search
CPC ....... F04F 1/10; G01N 33/5302; G01N 35/02; G01N 35/10; G01N 35/1004; G01N 35/1095
See application file for complete search history.

(56) References Cited

FOREIGN PATENT DOCUMENTS

| | | | |
|---|---|---|---|
| CN | 104111326 A | | 10/2014 |
| CN | 104436815 A | | 3/2015 |
| CN | 206570074 U | * | 10/2017 |
| WO | 2011083633 A1 | | 7/2011 |

OTHER PUBLICATIONS

International Search Report issued in corresponding International Application No. PCT/CN2017/120372, dated Sep. 18, 2018, 4 pages.

* cited by examiner

WASTE LIQUID TREATMENT APPARATUS, METHOD AND SAMPLE ANALYZER

CROSS-REFERENCE TO RELATED APPLICATIONS

This application is a bypass continuation of Patent Cooperation Treaty Application No. PCT/CN2017/120372, filed on Dec. 30, 2017, the content thereof is hereby incorporated by reference in its entirety. This application is related to U.S. application Ser. No. 16/898,426, filed on Jun. 10, 2020, which is a bypass continuation of Patent Cooperation Treaty Application No. PCT/CN2017/120371, filed on Dec. 30, 2017, the content thereof is also incorporated by reference in its entirety.

TECHNICAL FIELD

The present application relates to the technical field of sample testing and analysis, and in particular to a waste liquid treatment apparatus, a waste liquid treatment method, and a sample analyzer.

BACKGROUND

During a whole testing and analysis process of a sample analyzer, for example, a blood cell analyzer, a certain amount of waste liquid is generated in each testing channel, cleaning channel, etc., and the generated waste liquid is collected via a waste liquid pipe and is then discharged outside the sample analyzer. Since tests are usually performed parallelly in testing channels in a current sample analyzer, the testing speed is very fast. With the testing speed increased, waste liquid treatment becomes a limiting factor of testing speed. It is therefore crucial to increase the speed of waste liquid treatment. At present, for commonly used methods of collecting and discharging a waste liquid, the following solutions are used.

In solution I, in a waste liquid treatment apparatus 101 shown in FIG. 1, a waste liquid pump 11 is directly used to collect waste liquids in waste liquid pipes 1, 2, 3, . . . and then discharge the waste liquids outside a sample analyzer. In this solution, the structure is simple, and a single pump can be used to discharge waste liquids in multiple channels. However, this solution has the following disadvantages: 1. The waste liquid pump 11 has a flow limit, and thus a parallel waste discharge cannot be implemented for the waste liquid pipes 1, 2, 3, . . . . In addition, if a parallel liquid discharge is performed, one of the waste liquid pipes may be emptied before the other waste liquid pipes to cause a discharge failure of the other waste liquid pipes. As a result, liquid discharge of only a single channel can be supported, leading to low efficiency. 2. A waste liquid needs to flow through the waste liquid pump 11. A check valve in the waste liquid pump 11 tends to fail due to debris in the waste liquid, causing damage to the waste liquid pump 11.

In solution II, in a waste liquid treatment apparatus 102 shown in FIG. 2, a waste liquid temporary storage device such as a waste liquid chamber 13 with pressure switching is used to collect and discharge waste liquids in an analyzer. The waste liquid chamber 13 is connected to a pressure supply device (which is not shown and is usually a high flow air pump) by a control valve 12. When the waste liquid chamber 13 is switched to a negative pressure state, the waste liquid chamber 13 collects waste liquids in waste liquid pipes 1 to 8. When the waste liquid chamber 13 is switched to a positive pressure state, waste liquids are discharged to the outside by the waste liquid chamber 13. By means of this solution, waste liquids can be simultaneously collected in a plurality of channels. However, this solution has the following disadvantages: 1. Two steps need to be performed from generating a waste liquid to discharging the waste liquid, namely collecting a waste liquid in a waste liquid pipe, and emptying the waste liquid chamber 13. At the time of emptying the waste liquid chamber 13, the waste liquid chamber cannot collect waste liquids in the waste liquid pipes 1 to 8. It is assumed that the time required to collect waste liquids in the waste liquid pipes 1 to 8 is T1, the time required to empty the waste liquid chamber 13 is T2, and the time of a cycle of collecting a waste liquid and then discharging the waste liquid is T, then T is equal to T1+T2. Waste liquid collection cannot be performed within the time T2, so that the time of the entire waste liquid treatment cycle is extended by T2. In a blood cell analyzer, the testing speed of the analyzer is affected by the length of T.

SUMMARY

The present application provides a waste liquid treatment apparatus, a waste liquid treatment method, and a sample analyzer, so that a waste liquid generated during a test can be treated in time, thereby effectively shortening a waste liquid treatment cycle.

A first aspect of the present application provides a waste liquid treatment apparatus. The waste liquid treatment apparatus is used for treating waste liquids in a plurality of waste liquid pipes. The waste liquid treatment apparatus comprises:

at least two waste liquid chambers, each of the waste liquid chambers being in communication with at least one waste liquid pipe, and each waste liquid chamber being used for collecting a waste liquid in the waste liquid pipe connected to the waste liquid chamber when the inside of the waste liquid chamber is in a negative pressure state;

a pressure supply device connected to the at least two waste liquid chambers and used for supplying air pressure to each waste liquid chamber; and a control device configured for controlling the pressure supply device to supply air pressure to each waste liquid chamber according to a preset air pressure timing corresponding to the waste liquid chamber, so that the inside of at least one waste liquid chamber is in a negative pressure state at any time during waste liquid treatment to collect a waste liquid.

A second aspect of the present application provides a waste liquid treatment apparatus. The waste liquid treatment apparatus is used for treating waste liquids in at least two groups of waste liquid pipes. The waste liquid treatment apparatus comprises:

at least two waste liquid chambers, each of the waste liquid chambers being in communication with one group of waste liquid pipes, and each waste liquid chamber being used for collecting a waste liquid in the waste liquid pipe connected to the waste liquid chamber when the inside of the waste liquid chamber is in a negative pressure state and discharging the collected waste liquid when the inside of the waste liquid chamber is in a positive pressure state;

a pressure supply device connected to the at least two waste liquid chambers and used for supplying air pressure to each waste liquid chamber; and a control device configured for controlling the pressure supply device to alternately supply negative pressure and positive pressure to each waste liquid chamber according to a preset air pressure timing corresponding to the waste liquid chamber, so that the inside of the waste liquid chamber is alternately in a negative pressure state and in a positive pressure state to alternately collect and discharge a waste liquid, and the waste liquid treatment apparatus is capable of simultaneously collecting and discharging a waste liquid during waste liquid treatment.

A third aspect of the present application provides a sample analyzer. The sample analyzer comprises a waste liquid source and the waste liquid treatment apparatus according to the first aspect or the second aspect of the present application. A waste liquid chamber of the waste liquid treatment apparatus is in communication with a discharge port of the waste liquid source by a plurality of waste liquid pipes. The waste liquid chamber is used for treating a waste liquid generated by the waste liquid source in communication with the waste liquid chamber.

A fourth aspect of the present application provides a waste liquid treatment method. The waste liquid treatment method comprises:

setting preset air pressure timings corresponding to at least two waste liquid chambers of a waste liquid treatment apparatus respectively, wherein each preset air pressure timing comprises a negative pressure period, and the negative pressure period corresponding to each waste liquid chamber corresponds to a waste discharge timing of a waste liquid source connected to the waste liquid chamber via a waste liquid pipe; and controlling the pressure supply device to supply air pressure to each waste liquid chamber according to the preset air pressure timing corresponding to the waste liquid chamber, so that the inside of at least one waste liquid chamber is in a negative pressure state at any time during waste liquid treatment to collect a waste liquid.

A fifth aspect of the present application provides a waste liquid treatment method. The waste liquid treatment method comprises:

setting preset air pressure timings corresponding to at least two waste liquid chambers of a waste liquid treatment apparatus respectively, wherein each preset air pressure timing comprises a negative pressure period and a positive pressure period, and the negative pressure period corresponding to each waste liquid chamber corresponds to a waste discharge timing of a waste liquid source connected to the waste liquid chamber via a waste liquid pipe; and controlling the pressure supply device to alternately supply negative pressure and positive pressure to each waste liquid chamber according to the preset air pressure timing corresponding to the waste liquid chamber, so that the inside of the waste liquid chamber is alternately in a negative pressure state and in a positive pressure state to alternately collect and discharge a waste liquid, and the waste liquid treatment apparatus is capable of simultaneously collecting and discharging a waste liquid during waste liquid treatment.

In the waste liquid treatment apparatus and method of the present application, at least two waste liquid chambers are used, and preset air pressure timings are appropriately set for the at least two waste liquid chambers, so that the at least two waste liquid chambers are capable of collecting waste liquids at different moments. In this way, a waste liquid generated during a test can be treated in time. In addition, it is ensured that at least one waste liquid chamber keeps collecting a waste liquid at any time during waste liquid treatment, so that a waste liquid treatment cycle can be effectively shortened, thereby helping increase the testing speed for a sample analyzer using the waste liquid treatment apparatus and the waste liquid treatment method.

BRIEF DESCRIPTION OF THE DRAWINGS

In order to illustrate technical solutions according to the embodiments of the present application or according to the prior art more clearly, a brief introduction to the drawings required for the description of the embodiments or the prior art will be provided below. Obviously, the drawings in the following description are only some of the embodiments of the present application, and those of ordinary skill in the art would also be able to obtain other drawings from these drawings without expending any inventive effort.

LIST OF REFERENCE SIGNS

Figure 1:
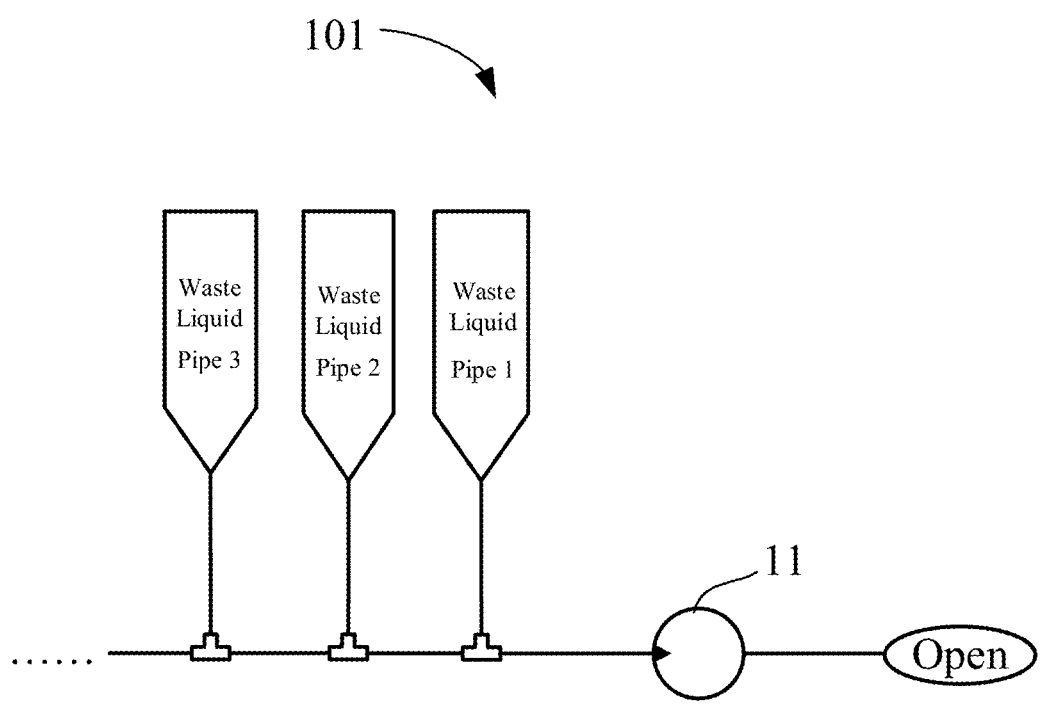
FIG. 1 is a schematic structural diagram of a waste liquid treatment apparatus in the prior art.
Figure 2:
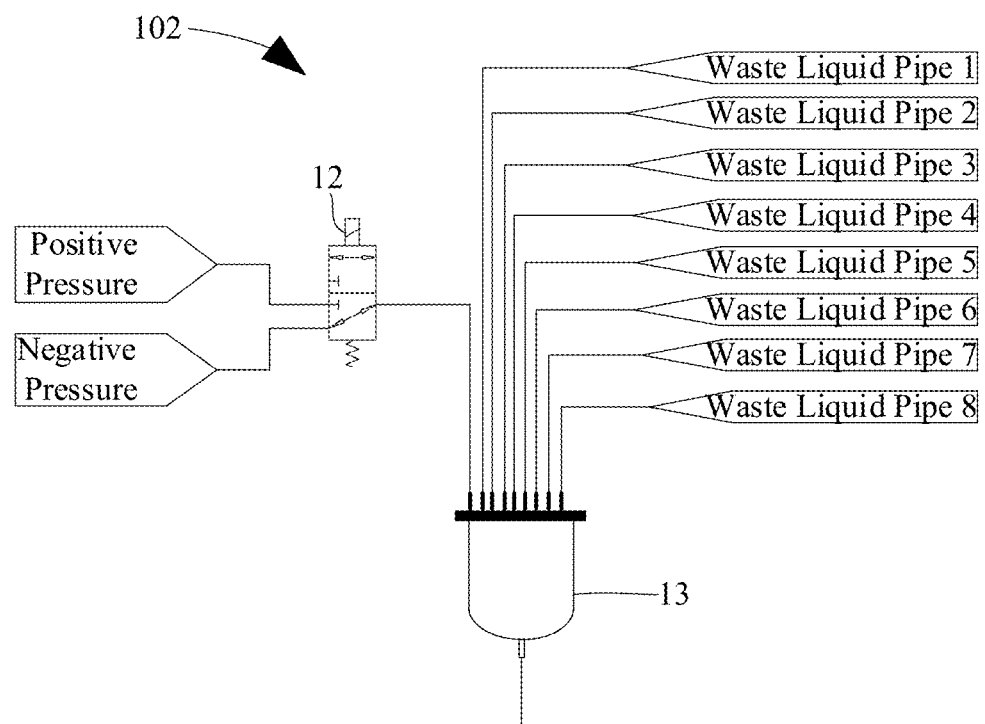
FIG. 2 is a schematic structural diagram of another waste liquid treatment apparatus in the prior art.

Waste liquid treatment apparatus 101, 102
Waste liquid pump 11
Control valve 12
Waste liquid chamber 13
Waste liquid treatment apparatus 200, 201
Waste liquid chamber 21, 21-1, 21-2
Body 211
Liquid outlet 2111
Cover 212
Liquid inlet 2121
Vent 2122
Guide tube 213
Plate 214
First plate 2141
Second plate 2142
Liquid level sensor 215
Connecting rod 216
Receiving cavity 217
Control device 22
Controller 221
Control valve 222, 222-1, 222-2
Waste discharge pipe 23
Connecting member 24, 25

Pressure supply device 30
Sample analyzer 400
Sample conveying system 41
Reagent compartment 42
Sample injection system 43
Cleaning system 44
Reaction system 45

The following detailed description will further explain the present application with reference to the above drawings.

DETAILED DESCRIPTION OF EMBODIMENTS

The technical solutions of the embodiments of the present application will be described below clearly and comprehensively in conjunction with the drawings of the embodiments of the present application. Obviously, the embodiments described are merely some embodiments of the present application and are not all the possible embodiments. Based on the embodiments given in the present application, all other embodiments that would be obtained by those of ordinary skill in the art without expending inventive effort shall all fall within the scope of protection of the present application.

Figure 3:
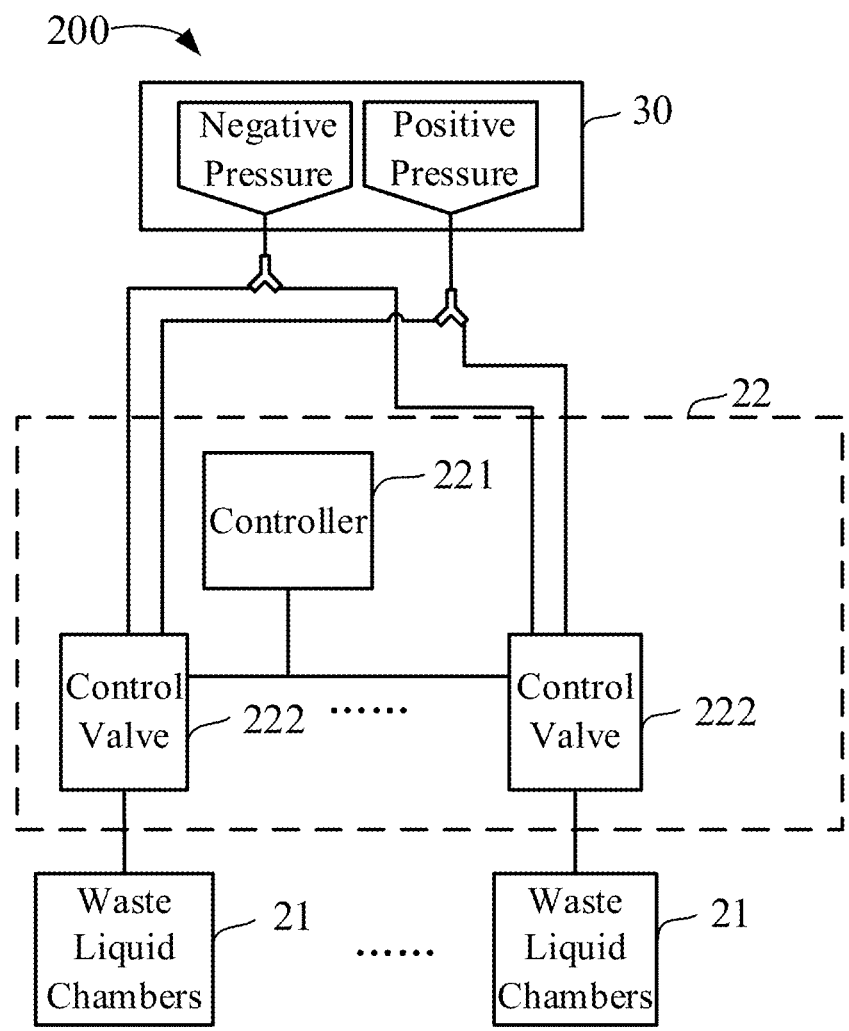
FIG. 3 is a principle block diagram of a waste liquid treatment apparatus according to an embodiment of the present application.

FIG. 3 is a principle block diagram of a waste liquid treatment apparatus 200 according to an embodiment of the present application. The waste liquid treatment apparatus 200 is used for treating waste liquids in a plurality of waste liquid pipes (not shown). It should be noted that "treating" of a waste liquid discussed in the present application comprises collecting and discharging a waste liquid. In this embodiment, the waste liquid treatment apparatus 200 comprises at least two waste liquid chambers 21, a control device 22, and a pressure supply device 30. Each waste liquid chamber 21 is in communication with at least one of the plurality of waste liquid pipes.

In another embodiment, the plurality of waste liquid pipes may be grouped in advance into at least two groups of waste liquid pipes. Each waste liquid chamber 21 is in communication with one group of waste liquid pipes. Each group of waste liquid pipes comprises one or more waste liquid pipes.

In this embodiment, the pressure supply device 30 is connected to the at least two waste liquid chambers 21 and is used for supplying air pressure to each waste liquid chamber 21. Each waste liquid chamber 21 is used for collecting a waste liquid in the waste liquid pipe connected to the waste liquid chamber when the inside of the waste liquid chamber is in a negative pressure state and discharging the collected waste liquid when the inside of the waste liquid chamber is in a positive pressure state. In this embodiment, a normal state of the inside of each waste liquid chamber 21 is a negative pressure state for collecting and storing a waste liquid.

The control device 22 is configured for controlling the pressure supply device 30 to supply air pressure to each waste liquid chamber 21 according to a preset air pressure timing corresponding to the waste liquid chamber 21, so that the inside of at least one waste liquid chamber 21 is in a negative pressure state at any moment during waste liquid treatment, to collect a waste liquid. Generally, the process of waste liquid collection is relatively slow, whereas the process of waste liquid discharge is relatively fast. Therefore, if it is ensured that waste liquids can be continuously collected during waste liquid treatment, the speed of waste liquid treatment can be greatly increased. In addition, if it is ensured that at least one waste liquid chamber 21 keeps collecting a waste liquid at any moment during waste liquid treatment, waste liquid collection and waste liquid discharge may be performed in parallel, so that a waiting time during serial performing of collection and discharge is avoided.

It may be understood that the preset air pressure timing may be written in a control program in advance or may be a manually set air pressure timing.

In addition, the control device 22 may further be configured for controlling the pressure supply device 30 to alternately supply negative pressure and positive pressure to each waste liquid chamber 21, so that the inside of the waste liquid chamber 21 is alternately in a negative pressure state and a positive pressure state to alternately collect and discharge a waste liquid, and the waste liquid treatment apparatus 200 is capable of simultaneously collecting a waste liquid and discharging a waste liquid during waste liquid treatment. For example, the control device 22 may control the pressure supply device 30 to supply air pressure to each waste liquid chamber 21, so that at any moment during waste liquid treatment, the inside of at least one waste liquid chamber 21 is in a negative pressure state to collect a waste liquid and the inside of at least one waste liquid chamber 21 is in a positive pressure state to discharge a waste liquid. In this way, waste liquids can be simultaneously collected and discharged at any moment. Alternatively, the control device 22 may control the pressure supply device 30 to supply air pressure to each waste liquid chamber 21, so that the inside of at least one waste liquid chamber 21 is in a positive pressure state at any moment during waste liquid treatment, to discharge a waste liquid. In this way, the waste liquid treatment apparatus can simultaneously collect and discharge waste liquids at a moment, thereby improving the efficiency of waste liquid treatment.

Specifically, in an embodiment, the preset air pressure timing comprises a negative pressure period and a positive pressure period. The control device 22 is configured for controlling the pressure supply device 30 to supply negative pressure to each waste liquid chamber 21 during the negative pressure period corresponding to the waste liquid chamber 21, and controlling the pressure supply device 30 to supply positive pressure to the waste liquid chamber 21 during the positive pressure period corresponding to the waste liquid chamber 21.

It may be understood that in an embodiment, the negative pressure periods corresponding to the at least two waste liquid chambers 21 may not overlap each another, so that only one waste liquid chamber is collecting a waste liquid at any moment during waste liquid treatment.

Figure 4:
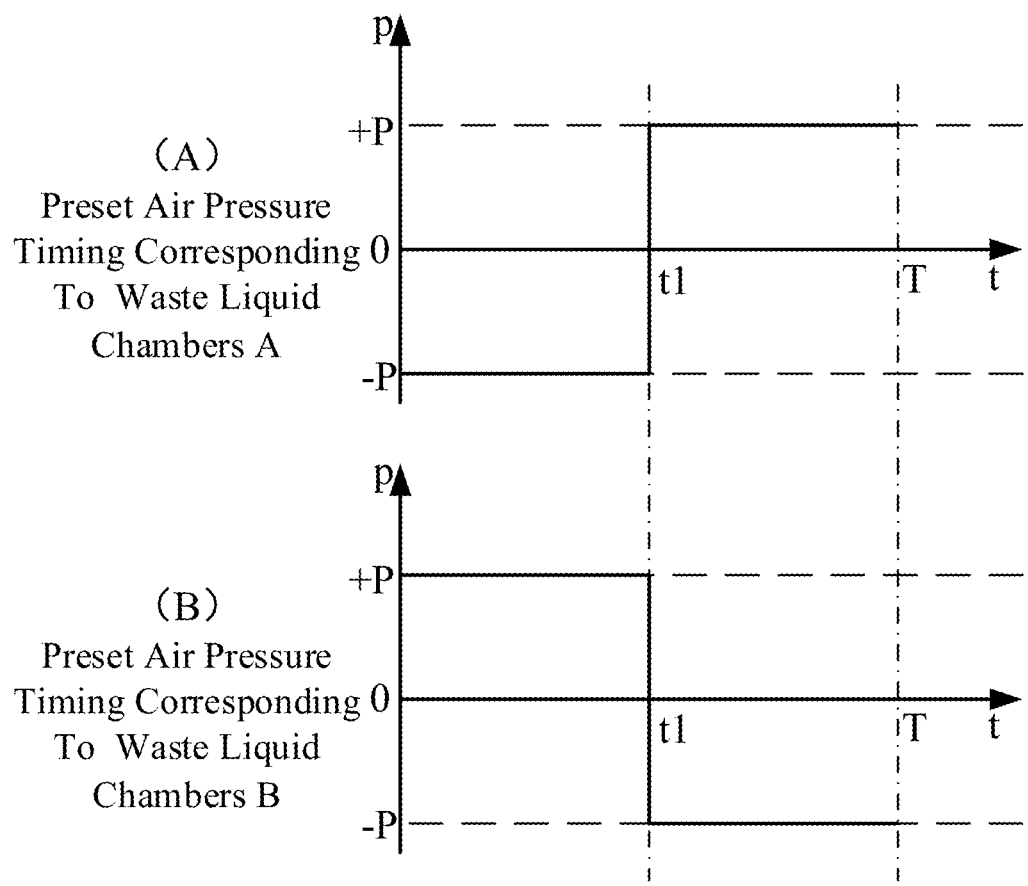
FIG. 4 is a schematic diagram of a preset air pressure timing corresponding to two waste liquid chambers of the waste liquid treatment apparatus in FIG. 3.

For example, as shown in FIG. 4, two waste liquid chambers A and B are taken as an example. Negative pressure periods corresponding to the two waste liquid chambers A and B do not overlap each another, so that only one waste liquid chamber A or B is collecting a waste liquid at any moment during waste liquid treatment. It may be understood that in another embodiment, positive pressure periods corresponding to the two waste liquid chambers A and B may not overlap each another, so that only one waste liquid chamber A or B is discharging a waste liquid at any moment during waste liquid treatment, and waste liquid collection and waste liquid discharge may take place simultaneously during waste liquid treatment.

Optionally, in another embodiment, the negative pressure periods corresponding to the at least two waste liquid chambers 21 may partially overlap each another, so that one or more waste liquid chambers 21 are collecting waste liquids at any moment during waste liquid treatment.

Figure 5:
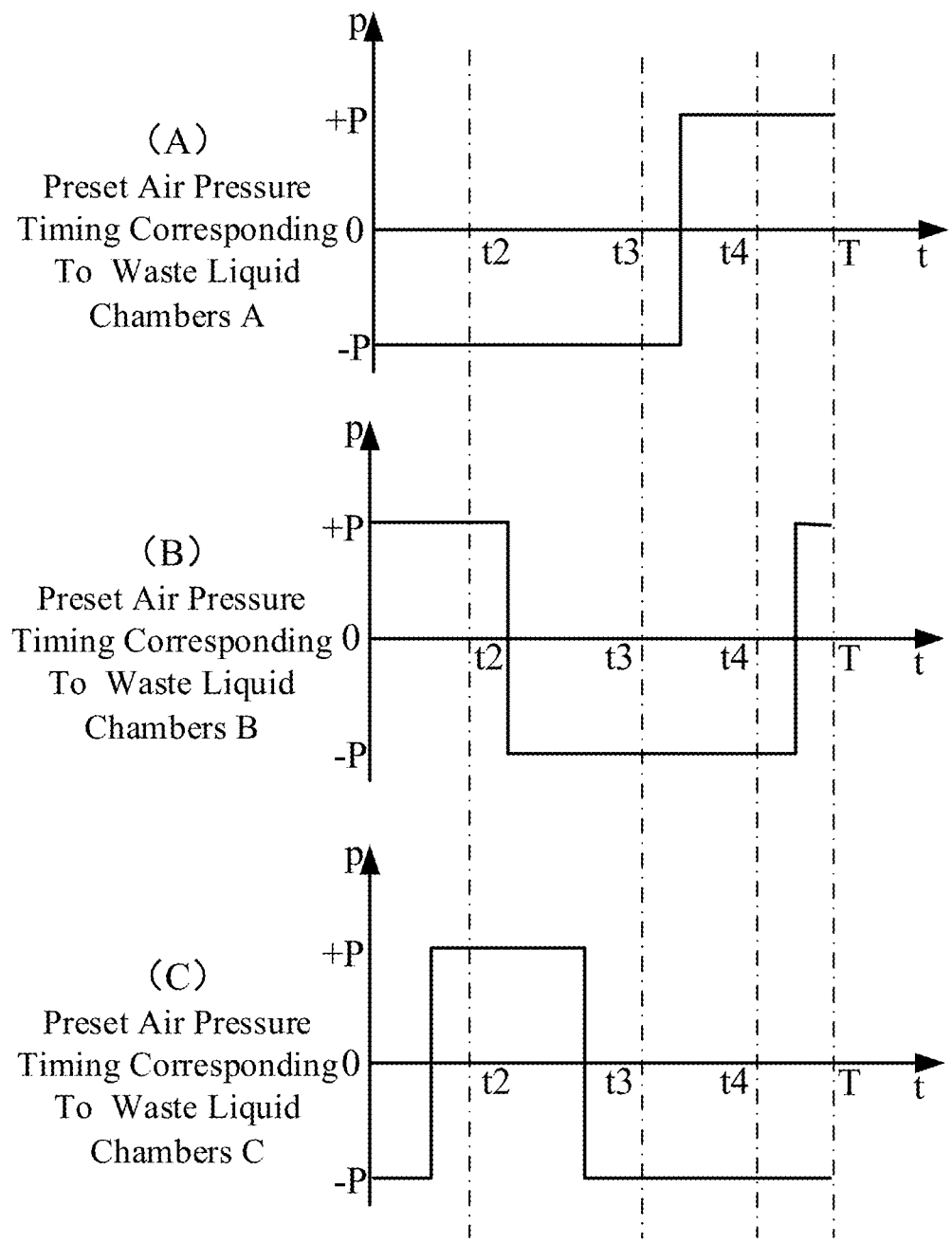
FIG. 5 is a schematic diagram of a preset air pressure timing corresponding to three waste liquid chambers of the waste liquid treatment apparatus in FIG. 3.

For example, as shown in FIG. 5, three waste liquid chambers A, B, and C are taken as an example. Negative pressure periods corresponding to the three waste liquid chambers A, B, and C partially overlap each another. At least one waste liquid chamber 21 is collecting a waste liquid at any moment during waste liquid treatment. For example, only the waste liquid chamber A is collecting a waste liquid at a moment t2. The waste liquid chambers A, B, and C are simultaneously collecting waste liquids at a moment t3. The waste liquid chambers B and C are collecting waste liquids at a moment t4. It may be understood that in another embodiment, positive pressure periods corresponding to three waste liquid chambers A, B, and C may partially overlap each other, so that at least one waste liquid chamber is discharging a waste liquid at any moment during waste liquid treatment. It may be understood that if it is ensured that at least one waste liquid chamber 21 is collecting and/or at least one waste liquid chamber is discharging a waste liquid at any moment during waste liquid treatment, the waste liquid treatment apparatus 200 may parallelly perform waste liquid collection and waste liquid discharge during waste liquid treatment.

Referring to FIG. 3 again, in an embodiment, the pressure supply device 30 comprises a negative pressure source and a positive pressure source. The negative pressure source is used for supplying negative pressure, and the positive pressure source is used for supplying positive pressure. In another embodiment, the pressure supply device 30 may be adjusted to generate negative pressure and positive pressure.

During waste liquid collection, the pressure supply device 30 may supply negative pressure to a waste liquid chamber 21 through an air pressure pipe. For example, the pressure supply device 30 generates negative pressure in the waste liquid chamber 21 by sucking air through the air pressure pipe. With the suction under negative pressure, a waste liquid generated by a waste liquid source connected to waste liquid chamber 21 via a waste liquid pipe is sucked into the waste liquid pipe from a discharge port of the waste liquid source, and is then sucked into the waste liquid chamber 21 from the waste liquid pipe.

In an embodiment, the control device 22 comprises a controller 221 and at least two control valves 222. Each control valve 222 is connected between the pressure supply device 30 and one waste liquid chamber 21. The controller 221 is connected to each control valve 222. The controller 221 is configured for controlling an on-state of each control valve 222, so as to control the pressure supply device 30 to supply air pressure to each waste liquid chamber 21, thus controlling a pressure status inside the waste liquid chamber 21. The controller 221 may be a microcontroller, a programmable logic controller (PLC) or any other controller.

In an embodiment, each control valve 222 at least comprises a negative pressure channel and a positive pressure channel. The controller 221 is configured for alternately opening the negative pressure channel and the positive pressure channel of each control valve 222, so as to control the pressure supply device 30 to alternately supply negative pressure and positive pressure to each waste liquid chamber 21.

Figure 6:
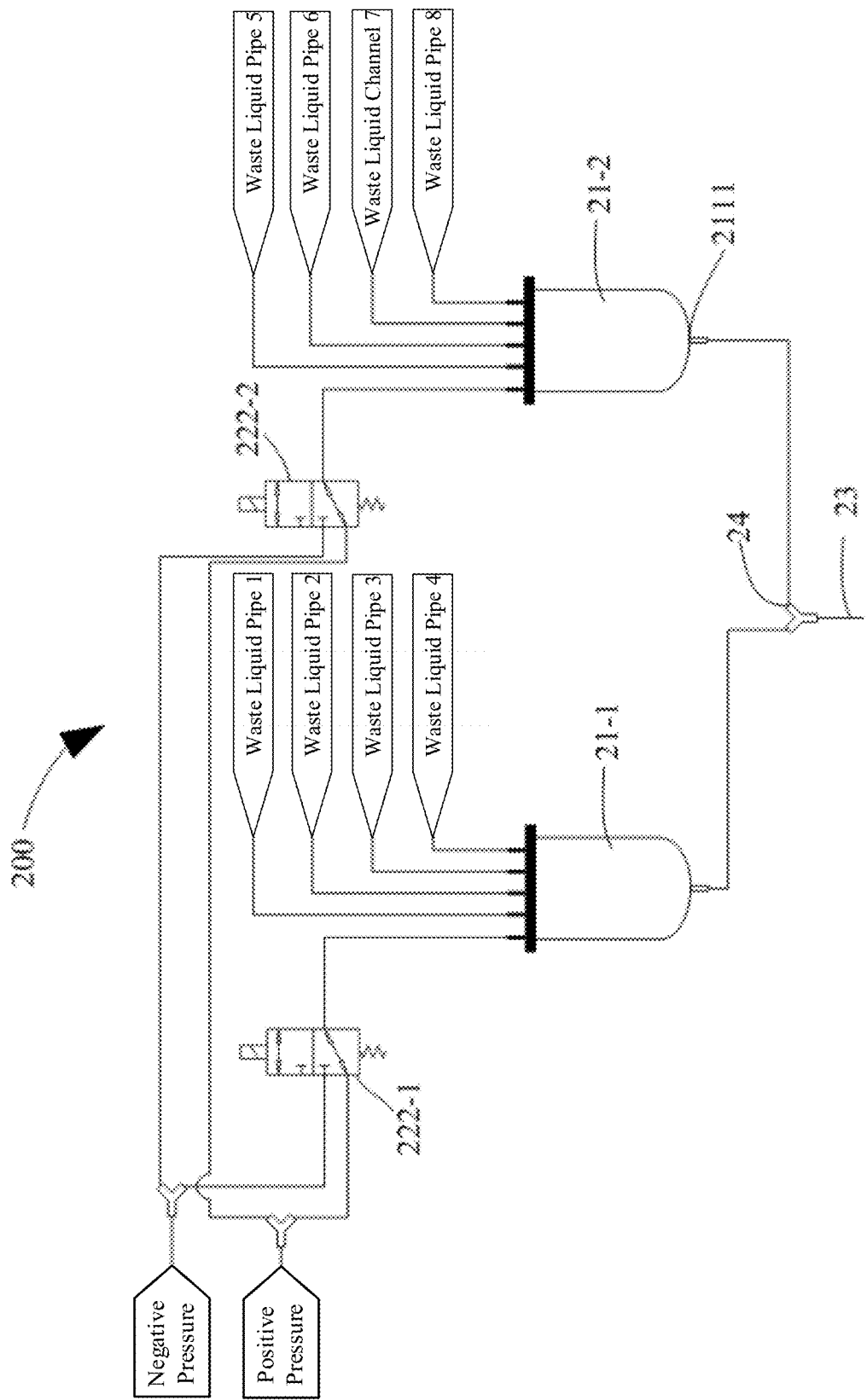
FIG. 6 is a schematic structural diagram of a waste liquid treatment apparatus according to a first embodiment of the present application.

Specifically, FIG. 6 is a schematic structural diagram of a waste liquid treatment apparatus 200 according to a first embodiment of the present application. In this embodiment, for the purpose of description, for example, the waste liquid treatment apparatus 200 comprises two waste liquid chambers 21-1 and 21-2 (namely a first liquid chamber 21-1 and a second liquid chamber 21-2), two control valves 222-1 and 222-2, and eight waste liquid pipes 1 to 8, and negative pressure periods of the two waste liquid chambers 21-1 and 21-2 do not overlap each other. The waste liquid chamber 21-1 is connected to the waste liquid pipes 1 to 4 respectively. The waste liquid chamber 21-2 is connected to the waste liquid pipes 5 to 8 respectively. The bottom of each of the waste liquid chambers 21-1 and 21-2 is provided with a liquid outlet 2111.

In a specific embodiment, during waste liquid treatment, when the negative pressure channel of the control valve 222-1 is opened, the waste liquid chamber 21-1 is in communication with a negative pressure air opening of the pressure supply device 30 and is disconnected from a positive pressure air opening of the pressure supply device. The inside of the waste liquid chamber 21-1 is in a negative pressure state, and the negative pressure state enables the waste liquid chamber 21-1 to collect waste liquids in the waste liquid pipes 1 to 4. Meanwhile, the positive pressure channel of the control valve 222-2 is opened. The waste liquid chamber 21-2 is disconnected from the negative pressure air opening of the pressure supply device 30 and is in communication with the positive pressure air opening of the pressure supply device. The inside of the waste liquid chamber 21-2 is in a positive pressure state, and the positive pressure state enables a waste liquid in the waste liquid chamber 21-2 to be discharged through the liquid outlet 2111 of the waste liquid chamber 21-2 into the outside.

Similarly, when the positive pressure channel of the control valve 222-1 is opened, the waste liquid chamber 21-1 is disconnected from the negative pressure air opening of the pressure supply device 30 and is in communication with the positive pressure air opening of the pressure supply device. The inside of the waste liquid chamber 21-1 is switched to a positive pressure state, and the positive pressure state enables a waste liquid in the waste liquid chamber 21-1 to be discharged through the liquid outlet 2111 of the waste liquid chamber 21-1 into the outside. Meanwhile, the on-state of the control valve 222-2 is switched to the negative pressure channel. The waste liquid chamber 21-2 is in communication with the negative pressure air opening of the pressure supply device 30 and is disconnected from the positive pressure air opening of the pressure supply device. The inside of the waste liquid chamber 21-2 is in a negative pressure state, and the negative pressure state enables the waste liquid chamber 21-2 to collect waste liquids in the waste liquid pipes 5 to 8.

It may be understood that in other embodiments, the quantity of the waste liquid chambers 21 is not limited to two, the quantity of the control valves 222 is not limited to two, and the quantity of the waste liquid pipes is not limited to eight.

In the waste liquid treatment apparatus 200 of the present application, the pressure supply device 30 is controlled to alternately supply negative pressure and positive pressure to each waste liquid chamber 21, so that waste liquids can be rapidly collected and discharged.

It may be understood that in other embodiments, with the speed of waste liquid discharge excluded from consideration, alternatively, the pressure supply device 30 may supply only negative pressure to the waste liquid chambers 21 to control the waste liquid chambers 21 to collect waste liquids. When the negative pressure in a waste liquid chamber 21 is released, the waste liquid in the waste liquid chamber 21 may be discharged through the liquid outlet 2111 of the waste liquid chamber 21 by gravity.

In the waste liquid treatment apparatus 200 of the present application, at least two waste liquid chambers 21 are used, and preset air pressure timings are appropriately set for the at least two waste liquid chambers. The waste liquid chambers 21 are then controlled to be alternately in a negative pressure state and a positive pressure state according to the preset timings. In this way, the waste liquid chambers can parallelly collect and discharge waste liquids in a plurality of waste liquid pipes. In addition, it is ensured that at least one waste liquid chamber keeps collecting a waste liquid at any moment during waste liquid treatment, so that a waste liquid treatment cycle can be effectively shortened, thereby increasing the testing speed for a testing device (for example, a sample analyzer) using the waste liquid treatment apparatus 200. In addition, the waste liquid treatment apparatus 200 of the present application has a simple structure and low production costs, thereby facilitating wide use of the waste liquid treatment apparatus 200 in various testing devices.

In an embodiment, one end of each of the plurality of waste liquid pipes is in communication with a discharge port of one of a plurality of waste liquid sources, the other end of said waste liquid pipe is in communication with a respective waste liquid chamber 21 according to a waste discharge timing of said waste liquid source connected to said waste liquid pipe, so that the negative pressure period corresponding to said waste liquid chamber 21 corresponds to a waste discharge timing of said waste liquid source connected to said waste liquid chamber via said waste liquid pipe, that is, the inside of the respective waste liquid chamber 21 is in a negative pressure state during the waste discharge time of said waste liquid source. For example, each waste liquid source has a respective waste discharge period. The waste discharge periods of the waste liquid sources may have different lengths and may be the same or different. The negative pressure period of each waste liquid chamber 21 may be set according to the waste discharge period of each waste liquid source. Waste liquid pipes in communication with the waste liquid sources may be appropriately allocated to respective waste liquid chambers according to the waste discharge periods of the waste liquid sources, so that negative pressure periods of the waste liquid chambers correspond to waste discharge periods of respective waste liquid sources. Therefore, the waste liquid chambers can be controlled as much as possible to collect waste liquids during waste discharge of the waste liquid sources and discharge collected waste liquids when the waste discharge of the waste liquid sources is paused or stopped.

In an embodiment, the other end of each waste liquid pipe is connected to only one respective waste liquid chamber 21 according to a waste discharge timing of a waste liquid source connected to the waste liquid pipe. For example, as shown in FIG. 6, the other ends of the waste liquid pipes 1 to 4 are connected to the waste liquid chamber 21-1, and the other ends of the waste liquid pipes 5 to 8 are connected to the waste liquid chamber 21-2. In other words, for the waste liquid source in communication with only one waste liquid chamber via a waste liquid pipe, the control device is configured for controlling the pressure supply device to supply negative pressure to the only one waste liquid chamber during a waste discharge period of the waste liquid source, so as to collect a waste liquid produced by the waste liquid source.

Figure 7:
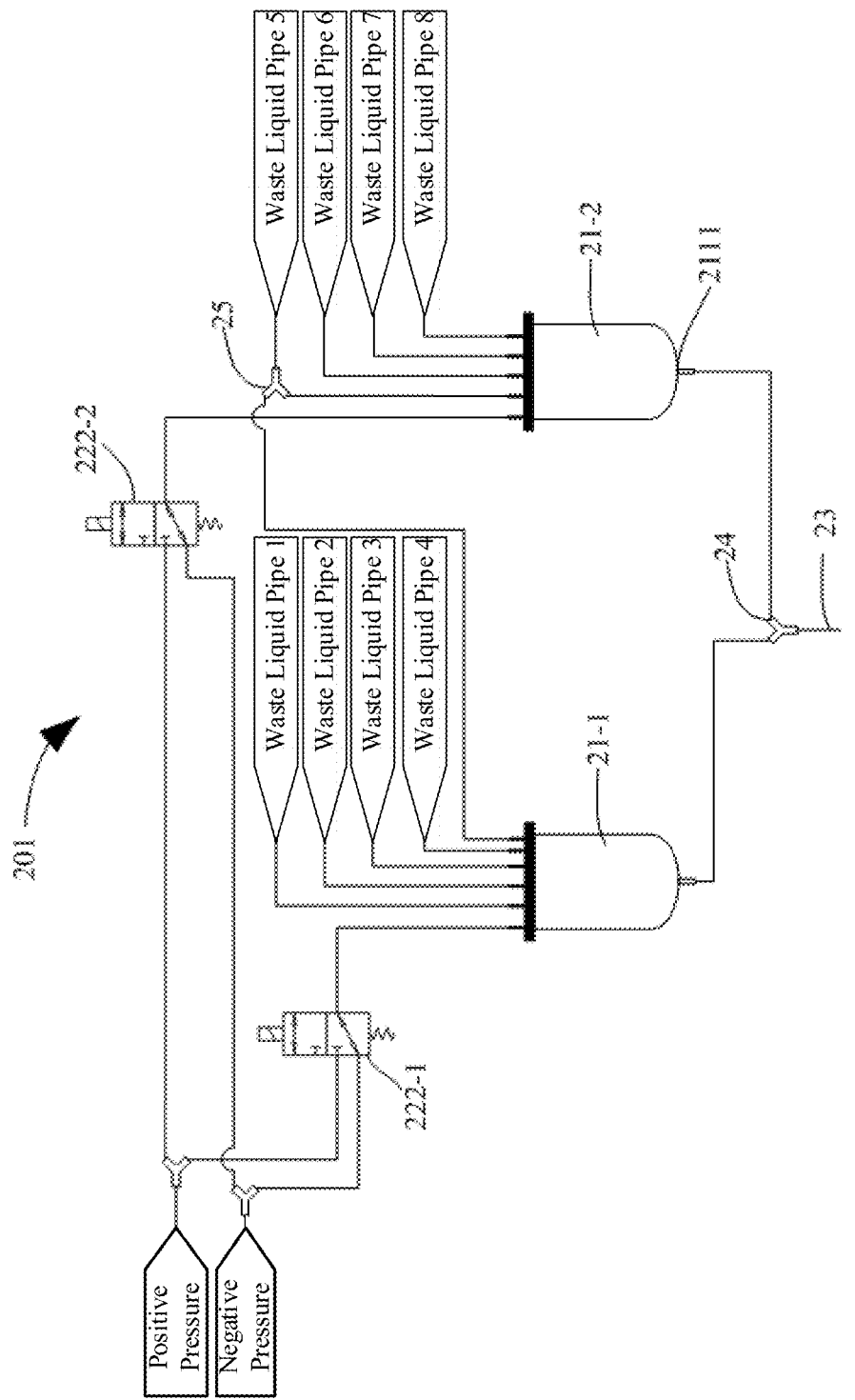
FIG. 7 is a schematic structural diagram of a waste liquid treatment apparatus according to a second embodiment of the present application.

In another embodiment, the other end of at least one of the plurality of waste liquid pipes is connected to more than one waste liquid chamber 21 according to a waste discharge timing of a waste liquid source connected to the at least one waste liquid pipe, and a sum of negative pressure periods corresponding to the more than one waste liquid chamber 21 corresponds to the waste discharge timing of the waste liquid source connected to the more than one waste liquid chamber via the same waste liquid pipe, that is, the inside of at least one of the more than one waste liquid chamber 21 is in a negative pressure state during the waste discharge time of the waste liquid source. For example, as shown in FIG. 7, in a waste liquid treatment apparatus 201, if a waste discharge period of a waste liquid source connected to a waste liquid pipe 5 is relatively long, the other end of the waste liquid pipe 5 may be connected to both the waste liquid chambers 21-1 and 21-2 by a connecting member 25 (for example, a three-way connector). A sum of negative pressure periods corresponding to the waste liquid chambers 21-1 and 21-2 corresponds to a waste discharge timing of the waste liquid source corresponding to the waste liquid pipe 5, thereby facilitating collection and discharge of a waste liquid in the waste liquid pipe 5 and shortening a waste liquid treatment cycle. In other words, for the waste liquid source in communication with more than one waste liquid chamber via a waste liquid pipe, the control device is configured for controlling the pressure supply device to supply negative pressure to at least one of the more than one waste liquid chambers during a waste discharge period of the waste liquid source, so as to collect a waste liquid produced by the waste liquid source.

In the waste liquid treatment apparatus 200 (201) of the present application, at least two waste liquid chambers 21 are disposed, and preset air pressure timings are arranged in combination, so that a waste liquid generated during a test can be discharged in time, thereby increasing the testing speed of the testing device.

A large variety and quantity of organic, inorganic, and biochemical reagents and solvents are used during tests by the testing device. As a result, waste liquids containing increasingly complex and varied components are generated and discharged. Various waste liquids, that enter a same waste liquid chamber and mix with each other, may react chemically with each other, and thus generate dirt, and the dirt accumulates in the waste liquid chamber after a long time of use, thus making maintenance more difficult.

In an embodiment, the other end of each waste liquid pipe may be connected to a respective waste liquid chamber 21 according to chemical properties of a waste liquid discharged by a waste liquid source connected to the waste liquid pipe, to separately discharge waste liquids capable of reacting chemically with each other and thus producing dirt into different waste liquid chambers 21.

In another embodiment, the plurality of waste liquid pipes may be grouped in advance into at least two groups of waste liquid pipes. Waste liquids discharged from waste liquid sources connected to each group of waste liquid pipes do not react chemically with each other and generate dirt after mixing with each other. Each waste liquid chamber 21 is in communication with one group of waste liquid pipes.

In this way, waste liquids with different chemical properties are separately collected, so that accidents that may occur after waste liquids with different chemical properties are mixed can be avoided, and pollution in the waste liquid chambers 21 caused by dirt generated after waste liquids are mixed can be reduced, thereby reducing maintenance difficulties and maintenance costs of the waste liquid chambers 21.

Figure 8:
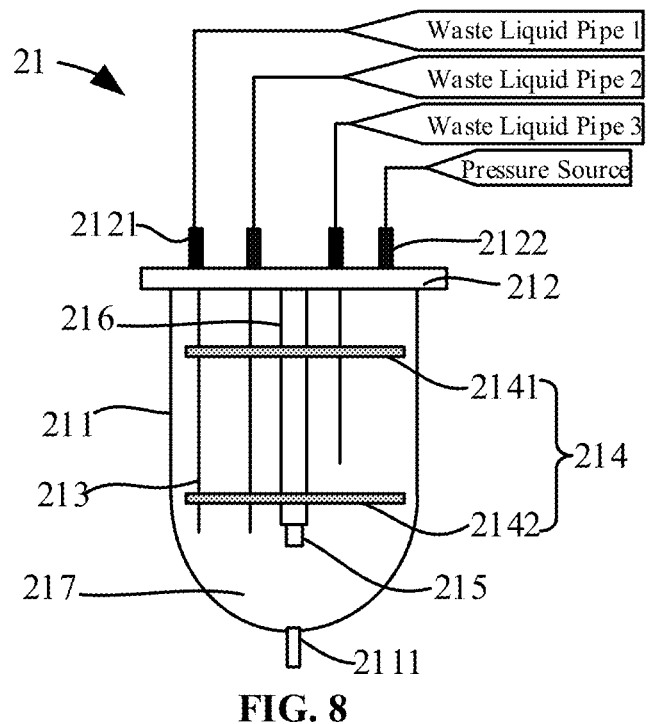
FIG. 8 is a schematic diagram of an internal structure of a waste liquid chamber according to an embodiment of the present application.

In an embodiment, the waste liquid treatment apparatus 200 (201) further comprises a liquid level sensor 215 (as shown in FIG. 8) disposed inside each waste liquid chamber 21. The controller 221 is further connected to each liquid level sensor 215. Each liquid level sensor 215 is used for sensing a liquid level height inside the waste liquid chamber 21 in which the liquid level sensor is located.

In an embodiment, the liquid level sensor 215 is a float sensor. The float sensor detects a liquid level by using the position of a float. When the liquid level rises to the position of the float, as the specific gravity of the float is less than that of the liquid to be detected, the float is supported and lifted by the liquid. When the liquid level falls below the position of the float, the float is suspended in the waste liquid chamber. It may be understood that the float sensor may generate different trigger signals corresponding to different states of the float, to report different liquid level heights.

In other embodiments, the liquid level sensor may be an electrode sensor. The electrode sensor detects a liquid level by determining whether two electrodes are connected. When the liquid level rises to the positions of the electrodes to enable both the electrodes to contact with the liquid, the electrodes are connected. When the liquid level falls below the positions of the electrodes, the electrodes are disconnected. It may be understood that the electrode sensor may generate different trigger signals corresponding to a connected state and a disconnected state of the electrodes, to report different liquid level heights.

To prevent the waste liquid inside the waste liquid chamber 21 from running into the vent 2122 due to the excessively large amount of the waste liquid (as shown in FIG. 8) and thus causing other accidents, in an embodiment, the controller 221 is further configured for controlling a duration for the pressure supply device 30 to supply negative pressure to each waste liquid chamber 21 within the negative pressure period corresponding to the waste liquid chamber 21 according to liquid level data sensed by the liquid level sensor 215 inside the waste liquid chamber 21, so as to control an amount of waste liquid in the waste liquid chamber 21.

Specifically, for each waste liquid chamber 21, the controller 221 is configured for controlling, when a liquid level height in the waste liquid chamber 21 sensed by the liquid level sensor 215 in the waste liquid chamber is greater than a first preset height, the pressure supply device 30 to temporarily stop supplying negative pressure to the waste liquid chamber 21 within the negative pressure period of the waste liquid chamber 21, such that the waste liquid chamber 21 temporarily stops collecting a waste liquid. The first preset height may be set as a safety height that prevents a waste liquid from running into the vent 2122. In other embodiments, the first preset height may be set as a safety height that prevents a waste liquid from overflowing from the waste liquid chamber 21. In other embodiments, the controller 221 may be further configured for controlling, when the liquid level height is greater than the first preset height, the pressure supply device 30 to supply positive pressure to the waste liquid chamber 21 within the negative pressure period of the waste liquid chamber 21, such that the waste liquid chamber 21 discharges a waste liquid.

The controller 221 may be connected to the pressure supply device 30. The controller 221 may be configured for controlling the pressure supply device 30 to temporarily stop supplying negative pressure to the waste liquid chamber 21 by closing the negative pressure air opening of the pressure supply device 30. Optionally, the controller 221 may be further configured for controlling the pressure supply device 30 to temporarily stop supplying negative pressure to the waste liquid chamber 21 by closing the negative pressure channel of the respective control valve 222. For example, the control valve 222 may further comprise a closed channel, and the controller 221 may be configured for switching the opened negative pressure channel of the respective control valve 222 to the closed channel, to disconnect the pressure supply device 30 from the waste liquid chamber 21, so as to control the pressure supply device 30 to temporarily stop supplying negative pressure to the waste liquid chamber 21.

It may be understood that, to reduce the air consumption of the system, liquid discharge under positive pressure in the waste liquid chamber 21 may not always performed in each cycle, or the duration of liquid discharge under positive pressure may be shortened according to an actual case, so that by means of designing the waste liquid chamber 21 to be large enough, waste liquids are consecutively collected multiple times and accommodated in the waste liquid chamber 21 and then liquid discharge under positive pressure is performed.

In an embodiment, the controller 221 is further configured for controlling a duration for the pressure supply device 30 to supply positive pressure to each waste liquid chamber 21 within the positive pressure period corresponding to the waste liquid chamber 21 according to liquid level data sensed by the liquid level sensor 215 inside the waste liquid chamber 21, to control an amount of waste liquid in the waste liquid chamber 21.

Specifically, for each waste liquid chamber 21, the controller 221 is configured for controlling, when a liquid level height in the waste liquid chamber 21 sensed by the liquid level sensor 215 in the waste liquid chamber 21 is less than a second preset height, the pressure supply device 30 to temporarily stop supplying positive pressure to the waste liquid chamber 21 within the positive pressure period of the waste liquid chamber 21, such that the waste liquid chamber 21 temporarily stops discharging a liquid. The second preset height may be set as a safety height higher than the liquid outlet 2111 to ensure that a particular amount of waste liquid is stored in the waste liquid chamber 21 and prevent the liquid outlet 2111 of the waste liquid chamber 21 from being in communication with the atmosphere to cause unnecessary air consumption of the system. It may be understood that the position of the liquid outlet 2111 may be set to be the lowermost position at the bottom of the waste liquid chamber 21.

In other embodiments, the controller 221 may be further configured for controlling, when the liquid level height is less than the second preset height, the pressure supply device 30 to supply negative pressure to the waste liquid chamber 21 within the positive pressure period of the waste liquid chamber 21, to continue collecting a waste liquid.

The controller 221 may be connected to the pressure supply device 30. The controller 221 may be configured for controlling the pressure supply device 30 to temporarily stop supplying positive pressure to the waste liquid chamber 21 by closing the positive pressure air opening of the pressure supply device 30. Optionally, the controller 221 may be further configured for controlling the pressure supply device 30 to temporarily stop supplying positive pressure to the waste liquid chamber 21 by closing the positive pressure channel of the respective control valve 222. For example, the control valve 222 may further comprise a closed channel. The control valve 221 may be configured for switching the opened positive pressure channel of the respective control valve 222 to the closed channel, to disconnect the pressure supply device 30 from the waste liquid chamber 21, so as to control the pressure supply device 30 to temporarily stop supplying positive pressure to the waste liquid chamber 21.

In other embodiments, the waste liquid treatment apparatus 200 (201) may further comprise a control switch connected to the liquid outlet 2111 of the waste liquid chamber 21. The controller 221 is configured for turning off the control switch when the inside of the waste liquid chamber 21 is in a negative pressure state, to prevent the liquid outlet 2111 of the waste liquid chamber 21 from communicating with atmosphere during waste liquid collection and thus from affecting the waste liquid collection.

In an embodiment, the waste liquid treatment apparatus 200 (201) further comprises a waste discharge pipe 23 connected to the liquid outlet 2111 of the waste liquid chamber 21. The waste discharge pipe 23 is used for discharging a waste liquid in the waste liquid chamber 21 connected to the waste discharge pipe into the outside.

In an embodiment, the waste liquid treatment apparatus 200 (201) comprises one waste discharge pipe 23. For example, as shown in FIG. 6 and FIG. 7, the one waste discharge pipe 23 is connected to the liquid outlet 2111 of each waste liquid chamber 21 by a connecting member 24 (for example, a three-way connector). The one waste discharge pipe 23 is used for discharging the waste liquid in each waste liquid chamber.

In another embodiment, the waste liquid treatment apparatus 200 (201) comprises a plurality of waste discharge pipes 23, and each waste discharge pipe 23 is connected to the liquid outlet 2111 of at least one waste liquid chamber 21. Each waste discharge pipe 23 is used for discharging a waste liquid in the waste liquid chamber connected to the waste discharge pipe. The plurality of waste discharge pipes 23 are used to separately discharge waste liquids collected by the waste liquid chambers 21, so as to avoid or reduce environmental pollution causing by dirt generated after the waste liquids in the waste liquid chambers 21 are mixed and react with each other.

The present application further provides a waste liquid chamber used for waste liquid treatment. FIG. 8 is a schematic diagram of the internal structure of a waste liquid chamber 21 according to an embodiment of the present application. The waste liquid chamber 21 comprises a body 211 and a receiving cavity 217 provided inside the body 211. The receiving cavity 217 is used for storing a waste liquid.

In an embodiment, the waste liquid chamber 21 further comprises at least one liquid inlet 2121, at least one vent 2122, and at least one liquid outlet 2111. The at least one liquid inlet 2121 and the at least one vent 2122 are disposed at an upper portion of the receiving cavity 217. The at least one liquid outlet 2111 is disposed at a lower portion of the receiving cavity 217. Each liquid inlet 2121 is connected to a waste liquid pipe, and a waste liquid may flow into the waste liquid chamber 21 through the waste liquid pipe and the corresponding liquid inlet 2121. The at least one liquid outlet 2111 is used for discharging a waste liquid in the waste liquid chamber 21.

There may be only one vent 2122. The positive pressure air opening and the negative pressure air opening of the pressure supply device may be connected to the only one vent 2122 by a same control valve. Switching between positive pressure and negative pressure in the waste liquid chamber can be realized by controlling the on-state of the control valve. Certainly, there may be two vents 2122. The positive pressure air opening and the negative pressure air opening of the pressure supply device are respectively connected to the two vents 2122 by a control valve. Switching between the positive pressure and the negative pressure in the waste liquid chamber can be realized by respectively controlling the on-states of the two control valves.

In an embodiment, as shown in FIG. 8 the body 211 is a cavity with one end open and the other end closed, the waste liquid chamber 21 further comprises a cover 212, and the cover 212 is used for closing the opening of the body 211. The shape and size of the body 211 and the cover 212 may be specifically designed as required, and are not specifically limited herein.

In an embodiment, the at least one liquid inlet 2121 and the at least one vent 2122 are both provided on the cover 212. The at least one liquid outlet 2111 is provided in a bottom wall of the body 211.

In other embodiments, the at least one liquid inlet 2121 and the at least one vent 2122 may both be provided at an upper portion of a side wall of the body 211. Alternatively, both the upper portion of the side wall of the body 211 and the cover 212 are provided with the liquid inlet 2121 and the vent 2122. In other embodiments, the outlet 2111 may be provided in the side wall of the body 211. Alternatively, the bottom wall of the body 211 and the side wall of the body 211 are both provided with the liquid outlet 2111.

In another embodiment, the body 211 is a closed cavity. It may be understood that in the other embodiment, the cover 212 may be omitted. In the embodiment, the top wall of the body 211 and/or the upper portion of the side wall of the body 211 is provided with the at least one liquid inlet 2121 and the vent 2122.

It may be understood that when the vent 2122 is provided in the side wall of the body 211, the vent 2122 should be provided as high as possible. For example, the vent 2122 should be as close to the top of the body 211 as possible.

In an embodiment, the waste liquid chamber 21 further comprises a first plate 2141 received in the receiving cavity 217. The first plate 2141 is located between the vent 2122 and the liquid outlet 2111 and located close to the vent 2122. It may be understood that the "close" herein refers to that, the first plate 2141 is located closer the vent 2122 than to the liquid outlet 2111 instead of attaching to the vent 2122.

In an embodiment, the waste liquid chamber 21 further comprises at least one guide tube 213 disposed inside the receiving cavity 217. Each guide tube 213 has a nozzle at one end of said guide tube 213 being in communication with part of the at least one liquid inlets 2121 or all of the at least one liquid inlet 2121 to introduce a waste liquid in the waste liquid pipe into the guide tube, and a nozzle at the other end of said guide tube 213 being disposed below the first plate 2141. The at least one guide tube 213 is used for guiding a waste liquid below the first plate 2141 in the receiving cavity 217. The first plate 2141 is used for preventing the waste liquid and/or a foam therefrom in the receiving cavity 217 from entering the vent 2122.

It may be understood that some of the liquid inlets 2121 may be used for connecting a liquid pipe with no waste liquid to flow through, for example, for connecting a liquid pipe for a hemolytic agent to flow through. To make it convenient for the hemolytic agent to enter the waste liquid chamber 21 to clean the receiving cavity 217 in the waste liquid chamber 21, the hemolytic agent should flow into the receiving cavity 217 from a position as high as possible in the waste liquid chamber 21. In an embodiment, the liquid inlet 2121 connected to the liquid pipe for the hemolytic agent to flow through may be provided in the side wall of the body 211 and located below the first plate 2141. In this case, the liquid inlet does not need to be connected to one of the at least one guide tube 213 in the receiving cavity 217. In this case, some liquid inlets 2121 are respectively connected to the nozzles at one ends of guide tubes 213, and other liquid inlets 2121 are not connected to any guide tube.

In another embodiment, the liquid inlet 2121 connected to the liquid pipe for the hemolytic agent to flow through may be provided above the first plate 2141, for example, provided in the cover 212 or in the top wall of the body 211. A guide tube 213 is used for connecting the liquid inlet 2121 in the receiving cavity 217, and the nozzle of the guide tube 213 is provided below the first plate 2141. In this case, each liquid inlet 2121 is connected to the nozzle at one end of a guide tube 213.

In the prior art, during waste liquid collection, under negative pressure, the waste liquid impacts the liquid surface at a high speed from the upper portion to the bottom of the receiving cavity 217, and the waste liquid tends to splash. In addition, a hemolytic agent or the like that contains a lot of surfactant tends to generate a lot of foam in the receiving cavity 217, and the foam accumulates above the liquid surface. When the waste liquid collected in the waste liquid chamber 21 gradually accumulates and the liquid lever rises, the splashed waste liquids and the foam may be sucked into the pressure supply device. Furthermore, since a waste liquid is collected in the waste liquid chamber 21 under negative pressure, during the suction under negative pressure, the foam generated in the receiving cavity 217 tends to be directly sucked into an air guide pipe through the vent 2122. This may cause damage to pneumatic components (for example, a negative pressure pump, a negative pressure valve, and a pneumatic pressure-regulating valve) in the pressure supply device. In the waste liquid chamber 21 of the present application, the first plate 2141 is disposed in the receiving cavity 217 and close to the vent 2122, and the guide tube 213 is used for guiding a liquid flowing from the liquid inlet 2121 below the first plate 2141, to isolate air interfaces from liquid interfaces inside the waste liquid chamber 21, so that the foam and/or the waste liquid is less likely to enter or is prevented from entering the air guide pipe, and the pneumatic components in the pressure supply device can be protected from damage, thereby solving the reliability problem of waste liquid treatment caused by the increase of testing speed of the testing device.

In an embodiment, the waste liquid chamber 21 further comprises a second plate 2142. The second plate 2142 is received in the receiving cavity 217 and located between the first plate 2141 and the liquid outlet 2111. That is, the first plate 2141 is located above the second plate 2142.

In an embodiment, multiple guide tubes 213 are provided, with nozzles at the other ends of the multiple guide tubes 213 being disposed above and/or below the second plate 2142 according to properties of the waste liquids guided by the multiple guide tubes, so as to introduce different waste liquids into the receiving cavity 217 at different heights. In other words, according to properties of the waste liquids guided by the multiple guide tubes, the nozzles at the other ends of part of the multiple guide tubes are disposed above the second plate, and the nozzles at the other ends of part of the multiple guide tubes are disposed below the second plate, so as to introduce different waste liquids into the first waste liquid chamber at different heights. For example, the nozzle at the other end of the guide tube that guides a waste liquid containing no blood is provided above the second plate 2142 to guide the waste liquid above the second plate 2142; and the nozzle at the other end of a guide tube that guides a waste liquid containing a high concentration of blood is provided below the second plate 2141 to guide the waste liquid below the second plate 2142. It may be understood that at this time the guide tubes may have different lengths, to guide waste liquids in different waste liquid pipes to positions at different heights in the waste liquid chamber for discharge.

In an embodiment, the waste liquid chamber 21 further comprises at least one third plate. The at least one third plate is received in the receiving cavity 217 and located between the first plate 2141 and the second plate 2142. The first, second, and third plates are disposed to separate, according to actual use, different liquids introduced into the receiving cavity 217 below different plates.

For example, the nozzle at the other end of the guide tube that guides a hemolytic agent is provided between the first plate 2141 and the third plate, so that the hemolytic agent is guided from a position as high as possible in the receiving cavity 217 into the receiving cavity 217 to clean the receiving cavity 217, and a foam generated from the hemolytic agent can be prevented from entering the vent 2122 at the same time; the nozzle at the other end of the guide tube that guides a waste liquid containing a low concentration of blood is provided between the third plate and the second plate 2142 to guide the waste liquid above the second plate 2142; and the nozzle at the other end of the guide tube that guides a waste liquid containing a high concentration of blood is provided below the second plate 2142 to guide the waste liquid below the second plate 2142.

In other embodiments, the nozzle at the other end of each guide tube 213 may be disposed below the second plate 2142. In this way, the position of the nozzle at the other end of each guide tube may be disposed as low as possible, for example, as close to the liquid outlet 2111 at the bottom of the waste liquid chamber 21 as possible, so that a waste liquid can be introduced into the lower portion of the waste liquid chamber 21 to prevent the waste liquid from directly impacting the liquid surface, so that splashing of the waste liquid in the waste liquid chamber is minimized or avoided, and the generation of foam is also reduced.

In an embodiment, the other end of each guide tube 213 sequentially passes through one or more plates in the waste liquid chamber 21 from top to bottom such that the nozzle at the other end of the guide tubes is located below the plate through which the other end of the guide tube passes. The plates in the waste liquid chamber 21 are further used for holding the guide tube 213 passing through the plates to prevent the guide tube 213 from displacing in the receiving cavity 217 during waste liquid collection, so that waste liquid collection is not affected or other accidents are avoided. In other words, the other end of each guide tube 213 passes through the first plate 2141 of the waste liquid chamber 21 from top to bottom, such that the nozzle at the other end of the guide tube is located below the first plate 2141, and the first plate 2141 of the first waste liquid chamber 21 is further used for holding the guide tube passing through the first plate 2141; or the other end of each guide tube sequentially passes through the first plate 2141 and the second plate 2142 of the waste liquid chamber 21 from top to bottom, such that the nozzle at the other end of the guide tube is located below the second plate 2142, and the first plate 2141 and/or the second plate 2142 of the waste liquid chamber 21 is further used for holding the guide tube passing through the first plate 2141 and the second plate 2142.

In other embodiments, the other end of each guide tube 213 may extend toward the bottom of the receiving cavity 217 along an inner wall of the receiving cavity 217 such that the nozzle at the other end of the guide tube is located above or below the second plate 2142.

As discussed above, in the prior art, during waste liquid collection, a waste liquid impacts a liquid surface at a high speed from the upper portion to the bottom of the receiving cavity 217 under negative pressure. As a result, the waste liquid tends to splash, and the entire inner wall of the waste liquid chamber 21 would be in contact with the waste liquid. After long-term use, the entire inner wall of the waste liquid chamber 21 would be covered with dirt (for example, blood clots). Consequently, during the maintenance of the waste liquid chamber, the entire waste liquid chamber needs to be fully filled with a cleaning liquid. The maintenance is very difficult, and it is difficult to implement self-maintenance of the machine. Periodical manual maintenance is usually required, and the maintenance costs are thus increased.

In an embodiment, each plate in the waste liquid chamber 21 is used for preventing a waste liquid, that flows from the nozzle of the guide tube 213 located below the plate, from coming into contact with the inner wall of the receiving cavity 217 above the plate. For example, when the nozzle at the other end of the guide tube that guides a hemolytic agent is disposed between the first plate 2141 and the third plate, because the first plate 2141 is located between the vent 2122 and the liquid outlet 2111, that is, the vent 2122 is located above the first plate 2141, the first plate 2141 can prevent as many liquid drops of the hemolytic agent as possible from coming into contact with the inner wall of the body 211 above the first plate 2141. In this way, foams or liquid drops generated from the hemolytic agent can be less likely to enter the vent 2122. When the nozzle at the other end of the guide tube that guides a waste liquid containing a low concentration of blood is provided between the third plate and the second plate 2142, the third plate can prevent liquid drops of the waste liquid containing a low concentration of blood from coming into contact with the inner wall of the body 211 above the third plate, thereby reducing the pollution caused by the waste liquid to the body 211. When the nozzle at the other end of the guide tube that guides a waste liquid containing a high concentration of blood is provided below the second plate 2141, the second plate 2141 can prevent liquid drops of the waste liquid containing a high concentration of blood from coming into contact with the inner wall of the body 211 above the second plate 2142, thereby reducing the pollution caused by the waste liquid to the body 211.

In the waste liquid chamber 21 of the present application, at least one plate is disposed in the receiving cavity 217, so that a waste liquid would not come into contact with a large area of the inner wall of the body 211 above the plate. After long-term use, only the wall below the plate becomes dirty and thus needs to be maintained. In this way, reagent consumption required for maintenance is reduced, and the maintenance becomes easier.

In an embodiment, the waste liquid chamber 21 further comprises a connecting rod 216. One end of the connecting rod 216 is fixed on the top wall (for example, the top of the cover 212 or the body 211) of the receiving cavity 217, and the other end extends toward the bottom of the receiving cavity 217. Each plate in the waste liquid chamber 21 is sleeved on the connecting rod 216.

In an embodiment, the waste liquid chamber 21 further comprises a liquid level sensor 215 disposed inside the receiving cavity 217. The liquid level sensor 215 is used for sensing a liquid level height inside the waste liquid chamber 21.

In an embodiment, the liquid level sensor 215 is disposed on the connecting rod 216. In other embodiments, the liquid level sensor 215 may be disposed on the inner wall of the body 211 or disposed in the receiving cavity 217 in other manners.

The waste liquid chamber 21 and the waste liquid treatment apparatus 200 (201) of the present application are applicable to various testing devices that need to discharge a liquid, for example, an immunoassay analyzer, a blood cell analyzer, a biochemical analyzer, a blood coagulation analyzer, and a urine analyzer, etc.

Figure 9:
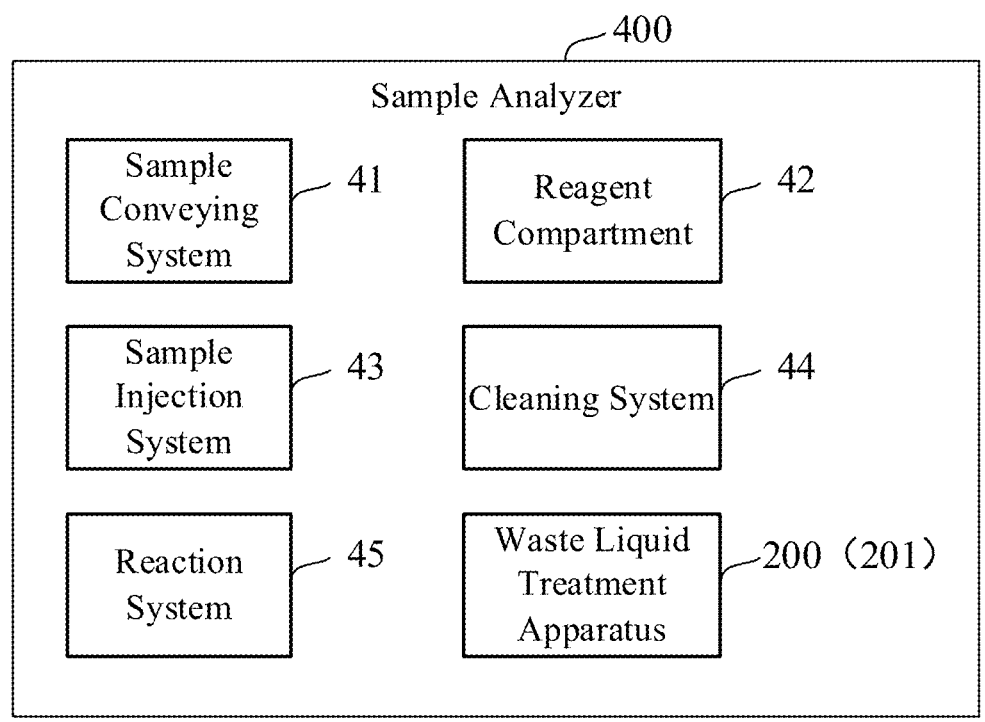
FIG. 9 is a principle block diagram of a sample analyzer according to an embodiment of the present application.

Based on the foregoing waste liquid chamber 21 and the waste liquid treatment apparatus 200 (201), the present application further provides a sample analyzer. FIG. 9 is a principle block diagram of a sample analyzer 400 according to an embodiment of the present application. The sample analyzer 400 may be an immunoassay analyzer, a blood cell analyzer, a biochemical analyzer, a blood coagulation analyzer, or a urine analyzer.

In an embodiment, the sample analyzer 400 at least comprises a sample conveying system 41, a reagent compartment 42, a sample injection system 43, a cleaning system 44, a reaction system 45, and the foregoing waste liquid treatment apparatus 200 (201). The sample conveying system 41 provides the sample analyzer 400 with a sample to be tested. The reagent compartment 42 provides the sample analyzer 400 with a reagent for use in a test. The sample injection system 43 is used for collecting the sample to be tested and the reagent, and injecting the collected sample and reagent into a reaction cell of the reaction system 45. The sample injection system 43 may comprise a moving mechanism and a sample injection needle. The sample injection needle is used for collecting a sample and a reagent. Each time after collecting a sample or reagent, the sample injection needle needs to be cleaned by the cleaning system 44. The cleaning system uses a cleaning liquid to clean the sample injection needle in a cleaning cell. A waste liquid generated after cleaning is discharged through the waste liquid treatment apparatus 200 (201). The sample conveying system 41, the reagent compartment 42, the sample injection system 43, the cleaning system 44, and the reaction system 45 are not the points to be improved in the present application. Details are not described herein.

In an embodiment, a waste liquid chamber 21 of the waste liquid treatment apparatus 200 (201) is in communication with a discharge port of a waste liquid source of the sample analyzer 400 by a plurality of waste liquid pipes. The waste liquid chamber 21 is used for treating waste liquids generated by the waste liquid source in communication with the waste liquid chamber.

In an embodiment, the waste liquid source of the sample analyzer 400 may be comprise at least one of the sample injection needle, a waste liquid discharge pipe of the reagent compartment, a magnetic separator disk or the reaction cell. It may be understood that the waste liquid source may be another component that needs to discharge a liquid in the sample analyzer 400.

Figure 10:
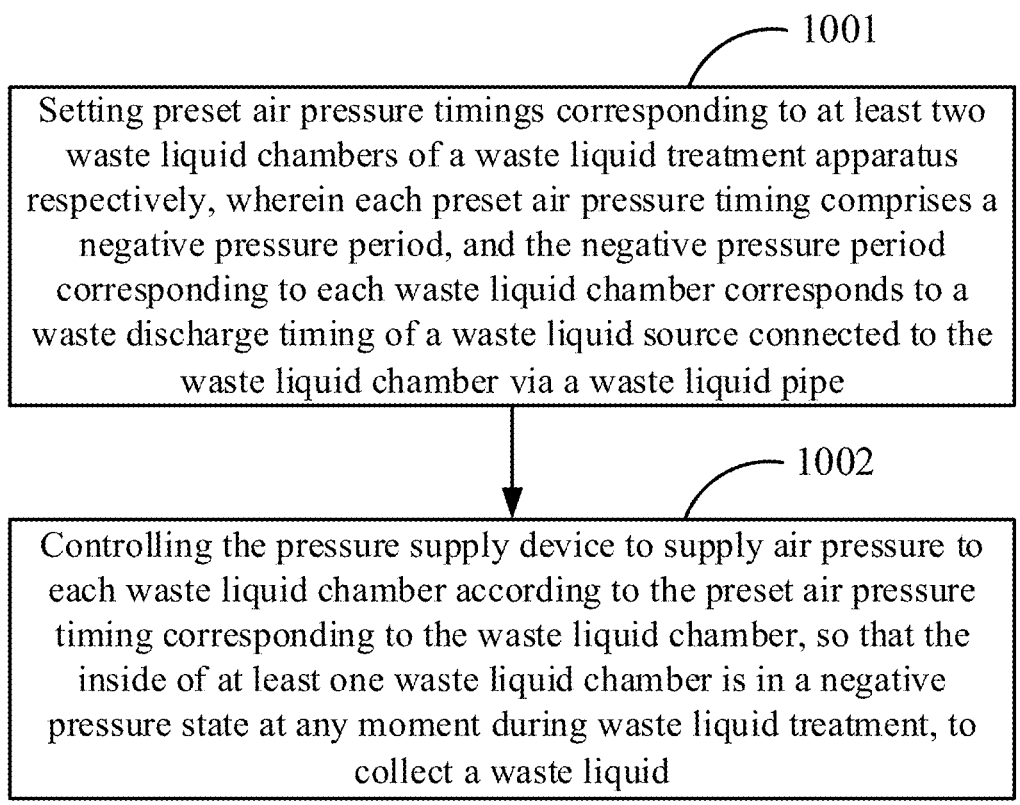
FIG. 10 is a schematic flowchart of a waste liquid treatment method according to a first embodiment of the present application.

Based on the foregoing waste liquid chamber 21 and the waste liquid treatment apparatus 200 (201), the present application further provides a waste liquid treatment method. FIG. 10 is a schematic flowchart of a waste liquid treatment method according to a first embodiment of the present application. It should be noted that the waste liquid treatment method in this embodiment of the present application is not limited to the steps and order in the flowchart shown in FIG. 10. According to different requirements, a step may be added to or removed from the steps in the flowchart or the order of the steps may be changed.

As shown in FIG. 10, the waste liquid treatment method comprises the following steps.

Step 1001, setting preset air pressure timings corresponding to at least two waste liquid chambers of a waste liquid treatment apparatus respectively, wherein each preset air pressure timing comprises a negative pressure period, and the negative pressure period corresponding to each waste liquid chamber corresponds to a waste discharge timing of a waste liquid source connected to the waste liquid chamber via a waste liquid pipe.

Step 1002, controlling the pressure supply device to supply air pressure to each waste liquid chamber according to the preset air pressure timing corresponding to the waste liquid chamber, so that the inside of at least one waste liquid chamber is in a negative pressure state at any moment during waste liquid treatment, to collect a waste liquid.

In an embodiment, the preset air pressure timing further comprises a positive pressure period, and the step of controlling the pressure supply device to supply air pressure to each waste liquid chamber according to the preset air pressure timing of the waste liquid chamber, comprises:

controlling the pressure supply device to alternately supply negative pressure and positive pressure to each waste liquid chamber according to the preset air pressure timing corresponding to the waste liquid chamber, so that the inside of the waste liquid chamber is alternately in a negative pressure state and a positive pressure state to alternately collect and discharge a waste liquid.

Further, in an embodiment, the step of controlling the pressure supply device to alternately supply negative pressure and positive pressure to each waste liquid chamber according to the preset air pressure timing corresponding to the waste liquid chamber comprises:

controlling the pressure supply device to supply negative pressure to the waste liquid chamber within the negative pressure period of the waste liquid chamber, and controlling the pressure supply device to supply positive pressure to the waste liquid chamber within the positive pressure period of the waste liquid chamber.

In an embodiment, the waste liquid treatment method further comprises: for each liquid chamber, obtaining liquid level data sensed by a liquid level sensor disposed inside the waste liquid chamber; and controlling a duration for the pressure supply device to supply negative pressure to the waste liquid chamber within the negative pressure period of the waste liquid chamber according to the liquid level data sensed by the liquid level sensor inside the waste liquid chamber, so as to control an amount of waste liquid in the waste liquid chamber.

Further, the step of controlling a duration for the pressure supply device to supply negative pressure to the waste liquid chamber according to the liquid level data sensed by the liquid level sensor inside the waste liquid chamber comprises:

if the liquid level data indicates that the liquid level height is greater than a first preset height, controlling the pressure supply device to temporarily stop supplying negative pressure to the waste liquid chamber such that the waste liquid chamber temporarily stops collecting a waste liquid.

In an embodiment, the waste liquid treatment method further comprises: for each waste liquid chamber obtaining liquid level data sensed by a liquid level sensor disposed inside the waste liquid chamber; and controlling a duration for the pressure supply device to supply positive pressure to the waste liquid chamber within the positive pressure period of the waste liquid chamber according to the liquid level data sensed by the liquid level sensor inside the waste liquid chamber, so as to control an amount of waste liquid in the waste liquid chamber.

Further, the step of controlling a duration for the pressure supply device to supply positive pressure to the waste liquid chamber according to the liquid level data sensed by the liquid level sensor inside the waste liquid chamber comprises:

if the liquid level data indicates that the liquid level height is less than a second preset height, controlling the pressure supply device to temporarily stop supplying positive pressure to the waste liquid chamber such that the waste liquid chamber temporarily stops discharging a liquid.

In the waste liquid treatment method provided in this embodiment, at least two waste liquid chambers are used, and preset air pressure timings are appropriately set for the at least two waste liquid chambers, so that the at least two waste liquid chambers are capable of collecting waste liquids at different moments. In addition, it is ensured that at least one waste liquid chamber keeps collecting a waste liquid at any moment during waste liquid treatment, so that a waste liquid generated during a test can be treated in time to effectively shorten a waste liquid treatment cycle, thereby increasing the testing speed for a sample analyzer using the waste liquid treatment apparatus and method.

Generally, the process of waste liquid collection is relatively slow, whereas the process of waste liquid discharge is relatively fast. Therefore, if it is ensured that a waste liquid can be continuously collected during waste liquid treatment, the speed of waste liquid treatment can be greatly increased. In addition, if it is ensured that at least one waste liquid chamber keeps collecting a waste liquid at any moment during waste liquid treatment, waste liquid collection and waste liquid discharge may be performed in parallel, so that a waiting time during serial performing of collection and discharge is avoided.

Figure 11:
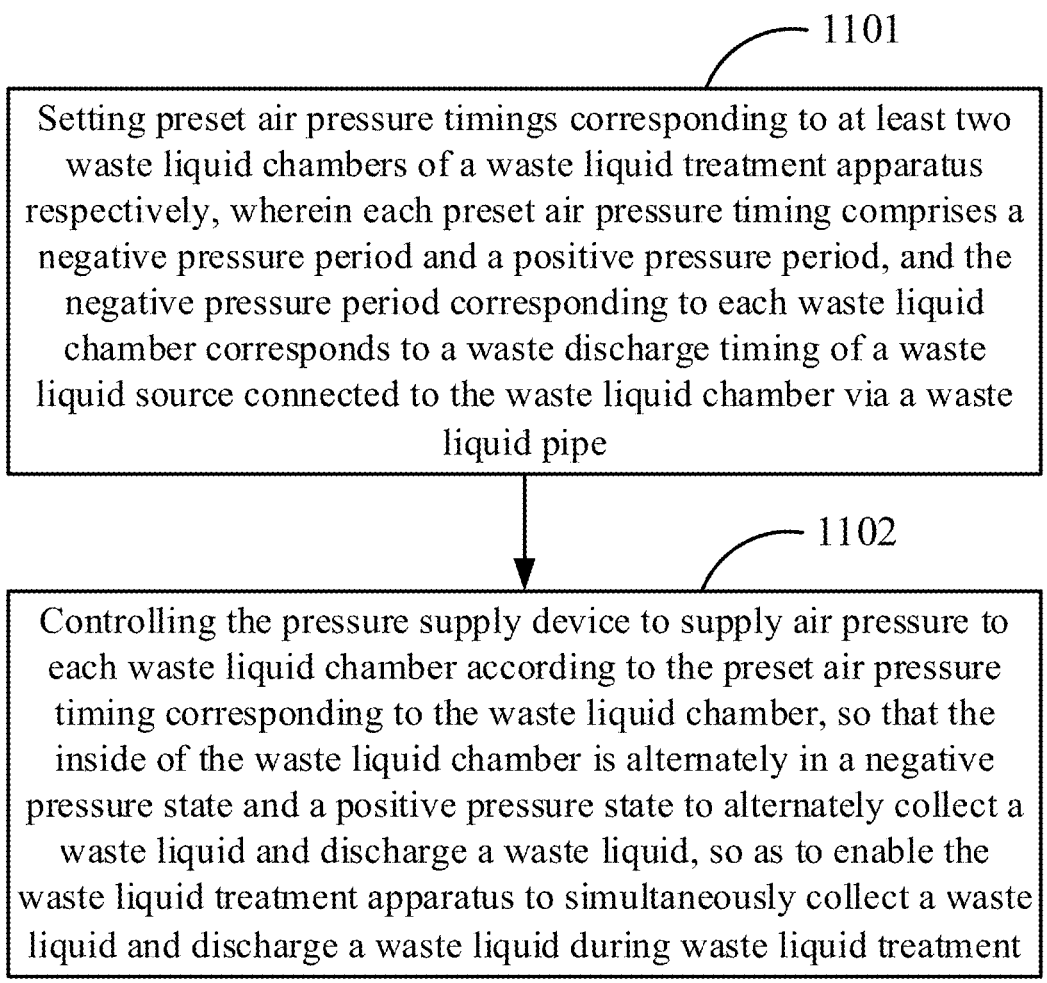
FIG. 11 is a schematic flowchart of a waste liquid treatment method according to a second embodiment of the present application.

Reference is made to FIG. 11, which is a schematic flowchart of a waste liquid treatment method according to a second embodiment of the present application. It should be noted that the waste liquid treatment method in this embodiment of the present application is not limited to the steps and order in the flowchart shown in FIG. 10. According to different requirements, a step may be added to or removed from the steps in the flowchart or the order of the steps may be changed.

As shown in FIG. 11, the waste liquid treatment method comprises the following steps.

Step 1101, setting preset air pressure timings corresponding to at least two waste liquid chambers of a waste liquid treatment apparatus respectively, wherein each preset air pressure timing comprises a negative pressure period and a positive pressure period, and the negative pressure period corresponding to each waste liquid chamber corresponds to a waste discharge timing of a waste liquid source connected to the waste liquid chamber via a waste liquid pipe.

Step 1102, controlling the pressure supply device to supply air pressure to each waste liquid chamber according to the preset air pressure timing corresponding to the waste liquid chamber, so that the inside of the waste liquid chamber is alternately in a negative pressure state and a positive pressure state to alternately collect a waste liquid and discharge a waste liquid, so as to enable the waste liquid treatment apparatus to simultaneously collect a waste liquid and discharge a waste liquid during waste liquid treatment.

For example, by controlling the air pressure supplied by the pressure supply device to each waste liquid chamber, at any moment during waste liquid treatment, the inside of at least one waste liquid chamber is in a negative pressure state to collect a waste liquid, and the inside of at least one waste liquid chamber is in a positive pressure state to discharge a waste liquid. In this way, waste liquids can be simultaneously collected and discharged at any moment. Alternatively, by controlling the air pressure supplied by the pressure supply device to each waste liquid chamber, the inside of at least one waste liquid chamber is in a positive pressure state at any moment during waste liquid treatment, to discharge a waste liquid. Therefore, at a moment, waste liquid collection and waste liquid discharge can be performed in parallel, thereby avoiding a waiting time during serial performing of waste liquid collection and waste liquid discharge. Further alternatively, and preferably, by controlling the air pressure supplied by the pressure supply device to each waste liquid chamber, the inside of at least one waste liquid chamber is in a negative pressure state at any moment during waste liquid treatment, to collect a waste liquid. Therefore, at a moment, waste liquid collection and waste liquid discharge can be performed in parallel, thereby avoiding a waiting time during serial performing of waste liquid collection and waste liquid discharge.

In an embodiment, the step of controlling the pressure supply device to supply air pressure to each waste liquid chamber according to the preset air pressure timing corresponding to the waste liquid chamber comprises:

controlling the pressure supply device to supply negative pressure to the waste liquid chamber within the negative pressure period corresponding to the waste liquid chamber, and controlling the pressure supply device to supply positive pressure to the waste liquid chamber within the positive pressure period corresponding to the waste liquid chamber.

In an embodiment, the waste liquid treatment method further comprises: for each waste liquid chamber, obtaining liquid level data sensed by a liquid level sensor disposed inside the waste liquid chamber; and controlling a duration for the pressure supply device to supply negative pressure to the waste liquid chamber within the negative pressure period corresponding to the waste liquid chamber according to the liquid level data sensed by the liquid level sensor inside the waste liquid chamber, to control an amount of waste liquid in the waste liquid chamber.

Further, the step of controlling a duration for the pressure supply device to supply negative pressure to the waste liquid chamber according to the liquid level data sensed by the liquid level sensor inside the waste liquid chamber, comprises:

if the liquid level data indicates that the liquid level height is greater than a first preset height, controlling the pressure supply device to temporarily stop supplying negative pressure to the waste liquid chamber such that the waste liquid chamber temporarily stops collecting a waste liquid.

In an embodiment, the waste liquid treatment method further comprises: for each waste liquid chamber, obtaining liquid level data sensed by a liquid level sensor disposed inside the waste liquid chamber; and controlling a duration for the pressure supply device to supply positive pressure to the waste liquid chamber within the positive pressure period corresponding to the waste liquid chamber according to the liquid level data sensed by the liquid level sensor inside the waste liquid chamber, to control an amount of waste liquid in the waste liquid chamber.

Further, the step of controlling a duration for the pressure supply device to supply positive pressure to the waste liquid chamber according to liquid level data sensed by the liquid level sensor inside the waste liquid chamber, comprises:

if the liquid level data indicates that the liquid level height is less than a second preset height, controlling the pressure supply device to temporarily stop supplying positive pressure to the waste liquid chamber such that the waste liquid chamber temporarily stops discharging a liquid.

In the waste liquid treatment method provided in the present application, at least two waste liquid chambers are used, and preset air pressure timings are appropriately set for the at least two waste liquid chambers. In this way, the waste liquid chambers can alternately and parallelly collect and discharge waste liquids in a plurality of waste liquid pipes, so that waste liquids generated during a test can be treated in time to effectively shorten a waste liquid treatment cycle, thereby increasing the testing speed for a sample analyzer using the waste liquid treatment apparatus and method.

For a person skilled in the art, apparently, the present application is not limited to the details in the foregoing exemplary embodiments, and the present application can be implemented in other specific forms without departing from the spirit or basic features of the present application. Therefore, from all perspectives, the embodiments should be considered to be exemplary and non-limitative. The scope of the present application is defined by the appended claims instead of the foregoing description. Therefore, all changes that fall within the meanings and scope of equivalent elements of the claims are intended to be covered by the present application. Any reference numeral in the claims should not be construed as limiting the related claims. In addition, apparently, the word "comprise" does not exclude other units or steps, and the singular reference of an element does not exclude the plural reference of such elements.

Finally, it should be noted that the foregoing embodiments are merely intended for describing the technical solutions of the present application rather than limiting the present application. Although the present application is described in detail with reference to the foregoing embodiments, persons of ordinary skill in the art should understand that they may still make modifications or equivalent replacements to the technical solutions of the present application without departing from the spirit and scope of the technical solutions of the embodiments of the present application.

What is claimed is:

1. A sample analyzer, comprising:
   a sample conveying system configured to provide a sample to be tested;
   a reagent compartment configured to provide a reagent for use in a test;
   a sample injection system configured to collect the sample to be tested and the reagent;
   a reaction system, wherein the sample injection system injects the collected sample and reagent into a reaction cell of the reaction system;
   a cleaning system configured to clean the sample injection system; and
   a waste liquid treatment apparatus comprising a plurality of waste liquid pipes, at least two waste liquid chambers, a pressure supply device and a control device, wherein each waste liquid chamber is in communication with a discharge port of at least one waste liquid source selected from the reagent compartment, the reaction system and the cleaning system via at least one of the waste liquid pipes, so as to treat a waste liquid produced by the at least one waste liquid source in communication with the waste liquid chamber,
   wherein each waste liquid chamber is in communication with at least one of the plurality of waste liquid pipes and is configured to collect the waste liquid in the waste liquid pipe connected to the waste liquid chamber when an inside of the waste liquid chamber is in a negative pressure state, the pressure supply device is connected to the at least two waste liquid chambers respectively and configured to supply air pressure to each waste liquid chamber, and the control device is configured for controlling the pressure supply device to supply air pressure to each waste liquid chamber according to a preset air pressure timing corresponding to the waste liquid chamber, the preset air pressure timings corresponding to the at least two waste liquid chambers each comprises a negative pressure period, and are configured so that at least one waste liquid chamber in the at least two waste liquid chambers corresponds to the negative pressure period at any time during collecting and discharging waste liquid, so that the inside of at least one waste liquid chamber is in a negative pressure state at any time during collecting and discharging waste liquid to collect the waste liquid.

2. The sample analyzer of claim 1, wherein each waste liquid chamber is further configured to discharge the collected waste liquid by gravity when the negative pressure in the waste liquid chamber is released; or
wherein each waste liquid chamber is further configured discharge the collected waste liquid when the inside of the waste liquid chamber is in a positive pressure state.

3. The sample analyzer of claim 2, wherein each waste liquid chamber is further configured to discharge the collected waste liquid when the inside of the waste liquid chamber is in a positive pressure state, and
wherein the control device is configured to control the pressure supply device to alternately supply negative pressure and positive pressure to each waste liquid chamber, so that the inside of the waste liquid chamber is alternately in a negative pressure state and in a positive pressure state to alternately collect and discharge the waste liquid.

4. The sample analyzer of claim 2, wherein each waste liquid chamber is further configured to discharge the collected waste liquid when the inside of the waste liquid chamber is in a positive pressure state, and
wherein the control device comprises a controller and at least two control valves, each control valve is connected between the pressure supply device and one waste liquid chamber, the controller is connected to each control valve, and the controller is configured to control the pressure supply device to supply air pressure to each waste liquid chamber via controlling an on-state of each control valve, so as to control the pressure status inside the waste liquid chamber.

5. The sample analyzer of claim 4, wherein each control valve comprises a negative pressure channel and a positive pressure channel, and the controller is configured to alternately open the negative pressure channel and the positive pressure channel of each control valve, so as to control the pressure supply device to alternately supply negative pressure and positive pressure to each waste liquid chamber.

6. The sample analyzer of claim 2, wherein each waste liquid chamber is further configured to discharge the collected waste liquid when the inside of the waste liquid chamber is in a positive pressure state, and the preset air pressure timing further comprises positive pressure period; and
wherein the waste liquid treatment apparatus further comprises a liquid level sensor disposed inside each waste liquid chamber, the control device is further connected to each liquid level sensor, and the controller is configured to control a duration for the pressure supply device to supply negative pressure or positive pressure to each waste liquid chamber within the negative pressure period or positive pressure period corresponding to the waste liquid chamber, according to liquid level data sensed by the liquid level sensor inside the waste liquid chamber, so as to control an amount of waste liquid in the waste liquid chamber.

7. The sample analyzer of claim 6, wherein for each waste liquid chamber, the control device is configured to control, when the liquid level sensor in the waste liquid chamber senses a liquid level height in the waste liquid chamber which is greater than a first preset height or less than a second preset height, the pressure supply device to temporarily stop supplying negative pressure or positive pressure to the waste liquid chamber within the negative pressure period or positive pressure period corresponding to the waste liquid chamber, so as to enable the waste liquid chamber to temporarily stop collecting the waste liquid or discharging the waste liquid.

8. The sample analyzer of claim 1, wherein a liquid outlet is provided at a bottom of each waste liquid chamber, and the waste liquid treatment apparatus further comprises:
a waste discharge pipe connected to the liquid outlets of the at least two waste liquid chambers, configured to discharge the waste liquid in the at least two waste liquid chambers; or
a plurality of waste discharge pipes, each connected to the liquid outlet of at least one waste liquid chamber and configured to discharge the waste liquid in the waste liquid chamber connected to the waste discharge pipe.

9. The sample analyzer of claim 1, wherein for the waste liquid source in communication with one waste liquid chamber via a waste liquid pipe, the control device is configured for controlling the pressure supply device to supply negative pressure to the one waste liquid chamber during a waste discharge period of the waste liquid source, so as to collect the waste liquid produced by the waste liquid source.

10. The sample analyzer of claim 1, wherein the waste liquid source is in communication with more than one waste liquid chamber via a waste liquid pipe, and the control device is configured to control the pressure supply device to supply negative pressure to at least one of the more than one waste liquid chambers during a waste discharge period of the waste liquid source, so as to collect the waste liquid produced by the waste liquid source.

11. The sample analyzer of claim 1, wherein one end of each waste liquid pipe is in communication with a discharge port of a waste liquid source, the other end of the waste liquid pipe is connected to a respective waste liquid chamber according to a chemical property of the waste liquid discharged by the waste liquid source connected to the waste liquid pipe, so as to separately discharge waste liquids capable of reacting chemically with each other into different waste liquid chambers.

12. The sample analyzer of claim 1, wherein at least one of the waste liquid chambers comprises:
a body;
a receiving cavity provided inside the body, configured to store the waste liquid;
at least one liquid inlet and at least one vent provided at an upper portion of the body, each liquid inlet being connected to a waste liquid pipe;
a liquid outlet provided at a lower portion of the body and used for discharging the waste liquid;
a first plate received in the receiving cavity, the first plate being located between the vent and the liquid outlet and located closer to the vent than to the liquid outlet; and
at least one guide tube, a nozzle at one end of each guide tube being in communication with part or all of the at least one liquid inlet to introduce the waste liquid into the guide tube, and a nozzle at the other end of the guide tube being disposed below the first plate, the guide tube being used for guiding the waste liquid into the receiving cavity, and the first plate being used for preventing the waste liquid or a foam therefrom in the receiving cavity from entering the vent.

13. The sample analyzer of claim 12, wherein the waste liquid chamber further comprises a second plate received in the receiving cavity and located between the first plate and the liquid outlet.

14. A waste liquid treatment method for a sample analyzer, wherein the sample analyzer comprises a sample conveying system, a reagent compartment, a sample injection system, a reaction system, a cleaning system, and a waste liquid treatment apparatus;
wherein the sample conveying system is used for providing a sample to be tested, the reagent compartment is used for providing a reagent for use in a test, the sample injection system is used for collecting the sample to be tested and the reagent and injecting the collected sample and reagent into a reaction cell of the reaction system, the cleaning system is used for cleaning the sample injection system, and the waste liquid treatment apparatus comprising a plurality of waste liquid pipes, at least two waste liquid chambers and a pressure supply device, wherein each waste liquid chamber is in communication with a discharge port of at least one waste liquid source selected from the reagent compartment, the reaction system and the cleaning system via at least one of the waste liquid pipes, so as to treat a waste liquid produced by the at least one waste liquid source in communication with the waste liquid chamber,
wherein the waste liquid treatment method comprises:
setting preset air pressure timings corresponding to the at least two waste liquid chambers respectively, wherein each preset air pressure timing comprises a negative pressure period, and the negative pressure period corresponding to each waste liquid chamber corresponds to a waste discharge timing of the waste liquid source connected to the waste liquid chamber via a waste liquid pipe; and
controlling the pressure supply device to supply air pressure to each waste liquid chamber according to the preset air pressure timing corresponding to the waste liquid chamber, wherein the preset air pressure timings corresponding to the at least two waste liquid chambers are configured so that at least one waste liquid chamber in the at least two waste liquid chambers corresponds to the negative pressure period at any time during collecting and discharging waste liquid, so that an inside of at least one waste liquid chamber is in a negative pressure state at any time during collecting and discharging waste liquid to collect the waste liquid.

15. The waste liquid treatment method of claim 14, wherein each preset air pressure timing further comprises a positive pressure period, and controlling the pressure supply device to supply air pressure to each waste liquid chamber according to the preset air pressure timing corresponding to the waste liquid chamber comprises:
controlling the pressure supply device to alternately supply negative pressure and positive pressure to each waste liquid chamber according to the preset air pressure timing corresponding to the waste liquid chamber, so that the inside of the waste liquid chamber is alternately in a negative pressure state and in a positive pressure state to alternately collect and discharge the waste liquid.

16. The waste liquid treatment method of claim 15, wherein controlling the pressure supply device to alternately supply negative pressure and positive pressure to each waste liquid chamber according to the preset air pressure timing corresponding to the waste liquid chamber comprises:
controlling the pressure supply device to supply negative pressure to the waste liquid chamber within the negative pressure period corresponding to the waste liquid chamber; and
controlling the pressure supply device to supply positive pressure to the waste liquid chamber within the positive pressure period corresponding to the waste liquid chamber.

17. The waste liquid treatment method of claim 14, further comprising: for each waste liquid chamber,
obtaining liquid level data sensed by a liquid level sensor disposed inside the waste liquid chamber; and
controlling a duration for the pressure supply device to supply negative pressure to the waste liquid chamber within the negative pressure period corresponding to the waste liquid chamber according to the liquid level data sensed by the liquid level sensor inside the waste liquid chamber, so as to control an amount of waste liquid in the waste liquid chamber.

18. The waste liquid treatment method of claim 17, wherein controlling a duration for the pressure supply device to supply negative pressure to the waste liquid chamber according to the liquid level data sensed by the liquid level sensor inside the waste liquid chamber further comprises:
if the liquid level data indicates that the liquid level height is greater than a first preset height, controlling the pressure supply device to temporarily stop supplying negative pressure to the waste liquid chamber, so as to enable the waste liquid chamber to temporarily stop collecting the waste liquid.

19. The waste liquid treatment method of claim 14, further comprising: for each waste liquid chamber,
obtaining liquid level data sensed by a liquid level sensor disposed inside the waste liquid chamber; and
controlling a duration for the pressure supply device to supply positive pressure to the waste liquid chamber within the positive pressure period corresponding to the waste liquid chamber according to the liquid level data sensed by the liquid level sensor inside the waste liquid chamber, so as to control an amount of waste liquid in the waste liquid chamber.

20. The waste liquid treatment method of claim 19, wherein controlling a duration for the pressure supply device to supply positive pressure to the waste liquid chamber according to the liquid level data sensed by the liquid level sensor inside the waste liquid chamber further comprises:
if the liquid level data indicates that the liquid level height is less than a second preset height, controlling the pressure supply device to temporarily stop supplying positive pressure to the waste liquid chamber, so as to enable the waste liquid chamber to temporarily stop discharging the waste liquid.

* * * * *